(12) United States Patent
Nakao et al.

(10) Patent No.: US 8,907,126 B2
(45) Date of Patent: Dec. 9, 2014

(54) TYROSINE DERIVATIVE AND METHOD FOR PRODUCING TYROSINE DERIVATIVE

(71) Applicant: NARD Institute, Ltd., Amagasaki (JP)

(72) Inventors: Hidekazu Nakao, Amagasaki (JP); Junichi Hoshino, Amagasaki (JP); Tokutaro Ogata, Kobe (JP); Naoki Miyashita, Amagasaki (JP); Yoshikazu Yamamoto, Amagasaki (JP)

(73) Assignees: Nard Institute, Ltd., Amagasaki-Shi, Hyogo (JP); Osaka University, Osaka (JP)

( * ) Notice: Subject to any disclaimer, the term of this patent is extended or adjusted under 35 U.S.C. 154(b) by 0 days.

(21) Appl. No.: 14/141,721

(22) Filed: Dec. 27, 2013

(65) Prior Publication Data

US 2014/0187814 A1 Jul. 3, 2014

Related U.S. Application Data

(60) Provisional application No. 61/746,648, filed on Dec. 28, 2012.

(30) Foreign Application Priority Data

Dec. 28, 2012 (JP) ................................. 2012-289111
Sep. 27, 2013 (JP) ................................. 2013-202199

(51) Int. Cl.
C07C 229/00 (2006.01)
C07C 229/36 (2006.01)
C07C 227/16 (2006.01)

(52) U.S. Cl.
CPC ............. *C07C 229/36* (2013.01); *C07C 227/16* (2013.01)
USPC ........................................................ 562/444

(58) Field of Classification Search
CPC .. C07C 229/36; C07C 229/22; C07C 229/34; C07C 229/38
See application file for complete search history.

(56) References Cited

U.S. PATENT DOCUMENTS

| 6,858,148 | B2 | 2/2005 | Warner et al. |
| 7,037,910 | B2 | 5/2006 | Ewing et al. |
| 7,241,381 | B2 | 7/2007 | Warner et al. |
| 7,378,418 | B2 | 5/2008 | Yu et al. |
| 7,519,145 | B2 | 4/2009 | Warner et al. |
| 7,816,357 | B2 | 10/2010 | Yu et al. |
| 7,858,385 | B2 | 12/2010 | Warner et al. |
| 7,929,662 | B2 | 4/2011 | Warner et al. |
| 2002/0028469 | A1 | 3/2002 | Burch et al. |
| 2003/0027129 | A1 | 2/2003 | Warner et al. |
| 2003/0101001 | A1 | 5/2003 | Huang |
| 2004/0017884 | A1 | 1/2004 | Havrilla et al. |
| 2004/0235059 | A1 | 11/2004 | Warner et al. |
| 2005/0011818 | A1 | 1/2005 | Warner et al. |
| 2005/0095636 | A1 | 5/2005 | Warner et al. |
| 2005/0143381 | A1 | 6/2005 | Yu et al. |
| 2005/0171110 | A1 | 8/2005 | Yu et al. |
| 2005/0192278 | A1 | 9/2005 | Ewing et al. |
| 2005/0214847 | A1 | 9/2005 | Havrilla et al. |
| 2007/0003008 | A1 | 1/2007 | Warner et al. |
| 2008/0102138 | A1 | 5/2008 | Bieley |
| 2008/0103111 | A1 | 5/2008 | Bieley |
| 2008/0107603 | A1 | 5/2008 | Aruoma |
| 2008/0220441 | A1 | 9/2008 | Birnbaum et al. |
| 2009/0175410 | A1 | 7/2009 | Warner et al. |
| 2010/0021570 | A1 | 1/2010 | Bieley |
| 2011/0014277 | A1 | 1/2011 | Bieley |
| 2011/0189161 | A1 | 8/2011 | Blum et al. |

FOREIGN PATENT DOCUMENTS

| JP | 2001-526021 A | 12/2001 |
| JP | 2003-194823 A | 7/2003 |
| JP | 2005-521707 A | 7/2005 |
| JP | 2007-514768 A | 6/2007 |
| JP | 2007-514770 A | 6/2007 |
| JP | 2010-509566 A | 3/2010 |
| JP | 2011-528321 A | 11/2011 |
| JP | 2012-230109 A | 11/2012 |
| JP | 2013-506678 A | 2/2013 |

OTHER PUBLICATIONS

Escoula et al. (New Journal of Chemistry, 1991, 15(1), 75).*

(Continued)

*Primary Examiner* — Fereydoun G Sajjadi
*Assistant Examiner* — Jennifer C Sawyer
(74) *Attorney, Agent, or Firm* — Bacon & Thomas, PLLC

(57) ABSTRACT

The objective of the present invention is to provide a tyrosine derivative which is useful as a melatonin $MT_1$ receptor antagonist, and a method for producing a specific tyrosine derivative with high yield by efficiently introducing an iodine atom at the para position of the phenolic hydroxy group in the benzene ring of tyrosine with good regioselectivity. The tyrosine derivative of the present invention is characterized in being represented by the following formula (I):

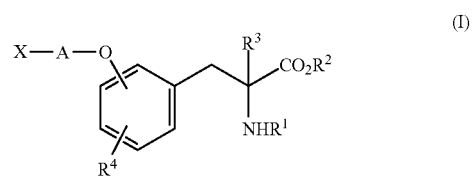

(I)

wherein $R^1$ is a protective group of the amino group and the like; $R^2$ is a protective group of the carboxy group and the like; $R^3$ is a hydrogen atom and the like; $R^4$ is a halogen atom and the like; A is $—(CH_2)_l—[Z(CH_2)_m]_n—$; X is a leaving group.

20 Claims, No Drawings

(56) References Cited

OTHER PUBLICATIONS

Bertin et al., "Grass roots chemistry: meta-Tyrosine, an herbicidal nonprotein amino acid", Proceedings of the National Academy of Sciences of the United States of America, 2007, vol. 104, No. 43, pp. 16964-16969.

Engman et al., "Toward Novel Antioxidants: Preparation of Dihydrotellurophenes and Selenophenes by Alkyltelluride-Mediated Tandem SRN1/SHi Reactions", J. Org. Chem., 1999, vol. 64, pp. 6764-6770.

"Explanation of Situation for Accelerated Examination" filed in JP 2013-202199 dated Oct. 31, 2013 and English translation thereof. List of Related Art, 2014.

* cited by examiner

TYROSINE DERIVATIVE AND METHOD FOR PRODUCING TYROSINE DERIVATIVE

CROSS-REFERENCE TO RELATED APPLICATIONS

This application is a non-provisional of U.S. Provisional Application No. 61/746,648 filed on Dec. 28, 2012, the contents of which are incorporated herein by reference. In addition, this application claims foreign priority to Japanese Patent Applications No. 2012-289111 filed on Dec. 28, 2012, and No. 2013-202199 filed on Sep. 27, 2013, the contents of which are incorporated herein by reference.

TECHNICAL FIELD

The present invention relates to a tyrosine derivative which is a melatonin $MT_1$ receptor antagonist, and a method for producing a tyrosine derivative with high yield by introducing an iodine atom at the para position to the position of the phenolic hydroxy group in the benzene ring of tyrosine with good regioselectivity.

BACKGROUND ART

Melatonin is a kind of indoleamine and synthesized from L-tryptophan through serotonin mainly in pineal organ. As a melatonin receptor, $MT_1$, $MT_2$ and $MT_3$ are known. A melatonin $MT_1$ receptor inhibits nerve firing in suprachiasmatic nucleus and has a function to induce sleep. It has been known that a melatonin $MT_1$ receptor antagonist has antidepressive activity.

Tyrosine is one kind of natural amino acids, and utilized as an amino acid which constitutes an enzyme and a structural protein in a living body and as a biologically active substance or the raw material compound thereof. For example, it is described in Non-patent Document 1 that m-tyrosine can be used as an herbicide to inhibit root growth of a plant. In addition, a tyrosine derivative is useful as a synthetic intermediate of various useful substances.

If an iodine atom can be introduced in a benzene ring of tyrosine, various compounds which are chemically or pharmaceutically useful can be synthesized from the thus obtained derivative by a functional group transformation reaction or the like, since an iodine atom is more reactive than a general chlorine atom and bromine atom among a halogen atom. For example, a compound which has an iodinated benzene ring can be utilized as a substance of Grignard reaction, Heck reaction and other coupling reaction.

When an iodine atom is introduced in a benzene ring of tyrosine, it is necessary to control the position of the iodine atom to be introduced. For example, it is described in Non-patent Document 2 that an iodine atom is introduced at the para position to the position of a protected phenolic hydroxy group of a benzene compound by reacting iodine with the benzene compound in the presence of silver trifluoroacetate.

PRIOR ART

Non-Patent Documents

Non-patent Document 1: Bertin C. et al., Proceedings of the National Academy of Sciences of the United States of America, 104(43), pp. 16964-16969 (2007)
Non-patent Document 2: Lars Engman et al., J. Org. Chem., 64, pp. 6764-6770 (1999)

DISCLOSURE OF THE INVENTION

Problems to be Solved by the Invention

As described above, it has been known that a melatonin $MT_1$ receptor antagonist has antidepressive activity. Therefore, a compound which has antagonistic activity against a melatonin $MT_1$ receptor is needed.

In addition, various availabilities of a tyrosine derivative have been found, and also a reaction to introduce an iodine atom in a benzene ring has been known. Therefore, it may be possible to obtain more useful tyrosine derivative by introducing an iodine atom in the benzene ring of tyrosine.

However, it is difficult to introduce an iodine atom at a specific position.

For example, in Scheme 5 on page 6769 of Non-patent Document 2 it appears as if an iodine atom was regioselectively introduced at the para position of an O-protected phenol derivative. In addition, it is also described that the yield thereof was 96%. However, in fact, the above yield relates to a mixture which was obtained by washing the reaction mixture and concentrating the washed mixture under reduced pressure, and does not relate to the purified target compound. The inventors of the present invention replicated the above example. As a result, the ratio of the target compound in which an iodine atom was introduced at the para position to the position of the phenolic hydroxy group was merely 89% in the reaction product, and a regioisomer in which an iodine atom was introduced at the ortho position was also produced at a ratio of 8%, and the yield of the mixture of the target compound and the regioisomer was merely 61%.

When a tyrosine derivative in which an iodine atom is regioselectively introduced in the benzene ring thereof is industrially mass-produced, a yield of 61% is never sufficient. If the yield can be increased by even several %, there are significant benefits in terms of a production cost particularly in industrial mass production.

In addition, if a regioisomer such as the above-described one is produced, it is difficult to remove such a regioisomer from the target compound and the regioisomer would be mixed in the target compound as impurity. Therefore, it is necessary to improve regioselectivity when an iodine atom is introduced at the specific position of the benzene ring of tyrosine.

Under the above-described circumstance, the objective of the present invention is to provide a tyrosine derivative which is useful as a melatonin $MT_1$ receptor antagonist, and a method for producing a specific tyrosine derivative with high yield by efficiently introducing an iodine atom at the para position to the position of the phenolic hydroxy group in the benzene ring of tyrosine with good regioselectivity.

Means for Solving the Problems

The inventors of the present invention intensively studied for solving the above problem. As a result, the inventors found that the specific tyrosine derivative exhibits antagonism against a melatonin $MT_1$ receptor. In addition, the inventors completed the present invention by finding that when iodination reaction of a phenol compound is carried out at −50° C. or lower whereas the corresponding temperature is 0° C. in the method described in Non-patent Document 2, the yield can be increased, far from decreasing, and regioselectivity of para position of phenolic hydroxy group can be improved.

The tyrosine derivative of the present invention is characterized in being represented by the following formula (I):

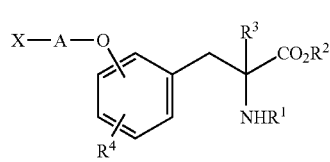

(I)

wherein $R^1$ is a hydrogen atom or a protective group for the amino group;

$R^2$ is a hydrogen atom or a protective group for the carboxy group;

$R^3$ is a hydrogen atom or a $C_{1-6}$ alkyl group;

$R^4$ is a halogen atom, a hydroxy group, a $C_{1-6}$ alkyl group, a $C_{1-6}$ halogenated alkyl group, an amino group, a mono($C_{1-6}$ alkyl) amino group, a di($C_{1-6}$ alkyl) amino group, an aryl group optionally having substituent α, a heterocyclic group optionally having substituent α, a $C_{1-6}$ alkoxy group, a $C_{1-6}$ alkylthio group, a $C_{1-6}$ halogenated alkoxy group or a $C_{7-13}$ aralkyloxy group optionally having substituent α;

A is $-(CH_2)_l-[Z(CH_2)_m]_n-$ wherein Z is an amino group, an ether group, a thioether group, a carbonyl group, a thionyl group, an ester group, an amide group, a urea group or a thiourea group; l is an integer of not less than 1 and not more than 6; m is an integer of not less than 1 and not more than 4; n is an integer of not less than 0 and not more than 4;

X is a leaving group selected from the group consisting of a chlorine atom, a bromine atom, an iodine atom, a methanesulfonyloxy group, a trifluoromethanesulfonyloxy group, a chloromethanesulfonyloxy group, an ethanesulfonyloxy group, a benzenesulfonyloxy group and a toluenesulfonyloxy group;

substituent α is one or more substituents selected from the group consisting of a halogen atom, a hydroxy group, a cyano group, a thiol group, an amino group, a mono($C_{1-6}$ alkyl) amino group, a di($C_{1-6}$ alkyl)amino group, a $C_{1-6}$ alkyl group, a $C_{1-6}$ alkoxy group, a $C_{1-6}$ halogenated alkyl group and a $C_{1-6}$ alkylthio group;

provided that the position of $R^4$ is para to the position of the X-A-O— group.

The tyrosine derivative of the present invention is exemplified by the tyrosine derivative represented by the following formula (I').

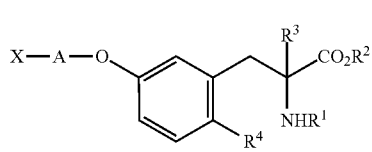

(I')

wherein $R^1$ to $R^4$, A and X are the same as the above.

In the tyrosine derivative of the present invention, $R^4$ is exemplified by a halogen atom, a hydroxy group, an aryl group optionally having substituent α, a heterocyclic group optionally having substituent α or a $C_{1-6}$ alkoxy group, and more specifically by a bromine atom or an iodine atom; and A is exemplified by $-(CH_2)_l-[O(CH_2)_m]_n-$.

The method for producing a tyrosine derivative represented by the following formula (III):

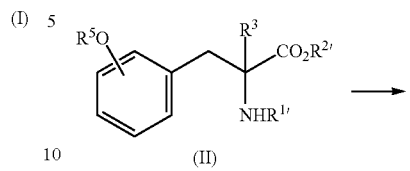

(II)

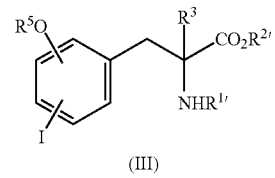

(III)

wherein $R^{1'}$ is a protective group of the amino group; $R^{2'}$ is a protective group of the carboxy group; $R^3$ is a hydrogen atom or a $C_{1-6}$ alkyl group; $R^5$ is a protective group of the phenolic hydroxy group; provided that the position of the iodine atom is para to the position of the $R^5O-$ group, is characterized in comprising the step of reacting the compound represented by the formula (II) with an iodination reagent at −50° C. or lower.

In the above-described production method of the tyrosine derivative (III), it is preferred that a combination of a molecular iodine and an iodination reaction accelerator is used as the iodination reagent, and silver trifluoroacetate or silver acetate is used as the iodination reaction accelerator.

The method for producing a tyrosine derivative represented by the following formula (I):

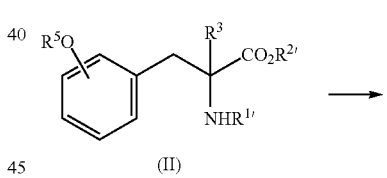

(II)

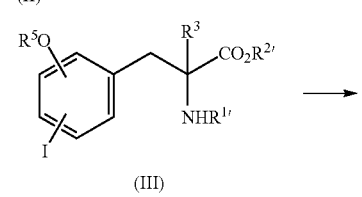

(III)

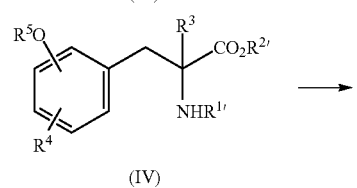

(IV)

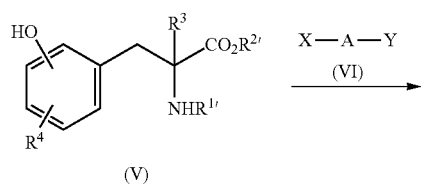

(V)

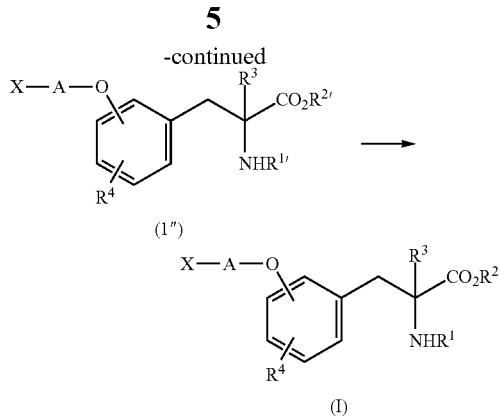

wherein

R$^1$ is a hydrogen atom or a protective group for the amino group;

R$^2$ is a hydrogen atom or a protective group for the carboxy group;

R$^{1'}$ is a protective group for the amino group;

R$^{2'}$ is a protective group for the carboxy group;

R$^3$ is a hydrogen atom or a C$_{1-6}$ alkyl group;

R$^4$ is a halogen atom, a hydroxy group, a C$_{1-6}$ alkyl group, a C$_{1-6}$ halogenated alkyl group, an amino group, a mono(C$_{1-6}$ alkyl) amino group, a di(C$_{1-6}$ alkyl) amino group, an aryl group optionally having substituent α, a heterocyclic group optionally having substituent α, a C$_{1-6}$ alkoxy group, a C$_{1-6}$ alkylthio group, a C$_{1-6}$ halogenated alkoxy group or a C$_{7-13}$ aralkyloxy group optionally having substituent α;

R$^5$ is a protective group of the phenolic hydroxy group;

A is —(CH$_2$)$_l$—[Z(CH$_2$)$_m$]$_n$— wherein Z is an amino group, an ether group, a thioether group, a carbonyl group, a thionyl group, an ester group, an amide group, a urea group or a thiourea group; l is an integer of not less than 1 and not more than 6; m is an integer of not less than 1 and not more than 4; n is an integer of not less than 0 and not more than 4;

X is a leaving group selected from the group consisting of a chlorine atom, a bromine atom, an iodine atom, a methanesulfonyloxy group, a trifluoromethanesulfonyloxy group, a chloromethanesulfonyloxy group, an ethanesulfonyloxy group, a benzenesulfonyloxy group and a toluenesulfonyloxy group;

Y is a hydroxy group or a leaving group selected from the group consisting of a chlorine atom, a bromine atom, an iodine atom, a methanesulfonyloxy group, a trifluoromethanesulfonyloxy group, a chloromethanesulfonyloxy group, an ethanesulfonyloxy group, a benzenesulfonyloxy group and a toluenesulfonyloxy group;

substituent α is one or more substituents selected from the group consisting of a halogen atom, a hydroxy group, a cyano group, a thiol group, an amino group, a mono(C$_{1-6}$ alkyl) amino group, a di(C$_{1-6}$ alkyl) amino group, a C$_{1-6}$ alkyl group, a C$_{1-6}$ alkoxy group, a C$_{1-6}$ halogenated alkyl group and a C$_{1-6}$ alkylthio group;

provided that the position of the iodine atom or R$^4$ is para to the position of the R$^5$O— group, the hydroxy group or X-A-O— group;

is characterized in comprising the steps of:

reacting the compound represented by the formula (II) with an iodination reagent at −50° C. or lower in order to obtain the compound represented by the formula (III);

transforming the iodine atom of the compound (III) to R$^4$ when R$^4$ of the compound (IV) is not an iodine atom in order to obtain the compound represented by the formula (IV);

removing the protective group of the phenolic hydroxy group of the compound (IV) in order to obtain the compound represented by the formula (V);

reacting the compound (V) with the compound represented by the formula (VI) in order to obtain the compound represented by the formula (I″); and removing the protective group of at least one of the amino group or the carboxy group if necessary in order to obtain the compound represented by the formula (I).

Effect of the Invention

According to the present invention, an iodine atom can be introduced at the para position of the phenolic hydroxy group in the benzene ring of a tyrosine derivative with high yield and high regioselectivity. Therefore, the present invention is useful particularly for industrial mass production of the tyrosine derivative in which an iodine atom is introduced at the above-described position, since the tyrosine derivative can be efficiently produced by the present invention.

In addition, the tyrosine derivative of the present invention has an actively reactive group in the substituent group at the phenolic hydroxy group and on the benzene ring, and therefore the tyrosine derivative is useful as a synthetic intermediate. Further, for example, the tyrosine derivative itself can be used as a non-naturally occurring amino acid for improving or modifying an activity of an enzyme such as t-PA by replacing a portion of the amino acids which constitute the enzyme with the tyrosine derivative. Furthermore, the tyrosine derivative can be used as a diagnostic agent and a bioimaging agent which utilizes in vivo redox reaction, a nitroxyl radical or the like. In particular, the tyrosine derivative of the present invention exhibits antagonism against a melatonin MT$_1$ receptor and is useful as a melatonin MT$_1$ receptor antagonist. Therefore, the tyrosine derivative of the present invention can be utilized as antidepressant agent or the like.

MODE FOR CARRYING OUT THE INVENTION

In the present invention method, tyrosine of which the amino group, the carboxy group and the phenolic hydroxy group are protected is preferably used as a raw material compound. Hereinafter, each step of the present invention method is described in order.

1. Protection Step of Amino Group

The order in which the amino group, the carboxy group and the phenolic hydroxy group are protected is not particularly limited. In general, the amino group is protected first, since the amino group can be easily protected and there are many kinds of suitable protective groups.

It is particularly preferred that a protective group for the amino group does not inhibit the after-described iodination reaction, and is not removed in the following reactions but can be easily removed in case of necessity. The protective group is exemplified by a carbamate-type protective group such as a t-butoxycarbonyl group, i.e. Boc group, a benzyloxycarbonyl group, i.e. Z group or Cbz group, a 2,2,2-trichloroethoxycarbonyl group, i.e. Troc group, an allyloxycarbonyl group, i.e. Alloc group, a methylcarbamate group, an ethylcarbamate group, a 9-fluorenylmethylcarbamate group, i.e. Fmoc group, a 9-(2-sulfo)fluorenylmethylcarbamate group, a 9-(2,7-dibromo) fluorenylmethylcarbamate group and a 4-methoxyphenacylcarbamate group; a sulfonamide-type protective group such as a p-toluenesulfonyl group, i.e. Ts group, and a 2-nitrobenzenesulfonyl group, i.e. a nosyl group or Ns group; an amide-type protective group such as a trifluoroacetyl group; a benzyl-type protective group; and a triphenylmethyl group, i.e. Tr group.

In addition, a cyclic protective group, which further reacts with —NH— group to form a ring including the nitrogen atom, can be used in the present invention. Such a cyclic protective group is exemplified by a 4,5-diphenyl-3-oxazoline-2-one group, a N-phthalimide group, an N-dithiasuccinimide group, a N-2,3-diphenylmaleimide group, a N-2,5-dimethylpyrrol group, a N-1,1,4,4-tetramethyldisilylazacyclopentane group, a 3-dimethyl-1,3,5-triazacyclohexane-2-one group and a 3,5-dinitro-4-pyridone group. The above-described protective groups are represented as a form including the nitrogen atom of the amino group to be protected.

In the tyrosine derivative (I) and the like of the present invention, there is a description of "—NHR$^{1\prime}$". However, the compound of which amino group is protected with two R's, in other words, the compound which has "—N(R$^1$)$_2$" is included in the range of the present invention.

When the protective group of the amino group is selected, the person skilled in the art can protect the amino group by ordinary method. For example, T. W. Green et al., "PROTECTIVE GROUPS IN ORGANIC SYNTHESIS" JOHN WILEY & SONS, INC. may be referred.

2. Protection Step of Carboxy Group

It is also preferred that a protective group for the carboxy group does not inhibit the after-described iodination reaction, and is not removed in the following reactions but can be easily removed in case of necessity. As such a protective group, an ester group such as a methoxymethyl ester group, a tetrahydropyranyl ester group and a t-butyl ester group can be used.

The person skilled in the art can protect the carboxy group by ordinary method similarly to the protection of the amino group.

3. Protection Step of Phenolic Hydroxy Group

It is also preferred that a protective group for the phenolic hydroxy group does not inhibit the after-described iodination reaction, and is not removed in the following reactions but can be easily removed in case of necessity. In addition, as described later, a substituent group may be introduced in the phenolic hydroxy group to obtain a derivative in some cases. Therefore, it is preferred that a protective group of the phenolic hydroxy group selectively removed while the amino group and the carboxy group are protected.

A protective group of the phenolic hydroxy group is exemplified by a silyl ether group selected from a trimethylsilyl group, a triethylsilyl group, a t-butyldimethylsilyl group, a triisopropylsilyl group and a t-butyldiphenylsilyl group.

The person skilled in the art can protect the phenolic hydroxy group by ordinary method similarly to the protection of the amino group and the carboxy group.

4. Iodination Step

The present invention method comprises the step of reacting the compound (II), of which the amino group, the carboxy group and the phenolic hydroxy group are protected in the above-described steps 1 to 3, with an iodination reagent at −50° C. or lower. In the present step, an iodine atom can be regioselectively introduced at the para position of the R$^5$O— group.

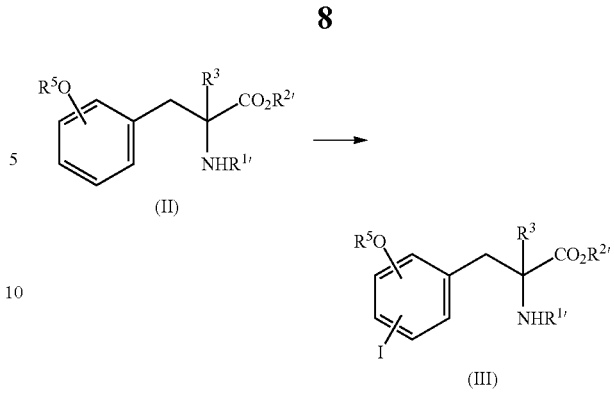

In the above scheme, R$^{1\prime}$, R$^{2\prime}$, R$^4$ and R$^5$ are the same as the above, and the position of the iodine atom in the compound (III) is para position of the R$^5$O— group.

The tyrosine derivative of the present invention is a m-tyrosine derivative or a o-tyrosine derivative, and preferably a m-tyrosine derivative, since an iodine atom is introduced at the para position of the phenolic hydroxy group or the protected phenolic hydroxy group in the present invention.

It is preferred that the above reaction is carried out in a solvent. Such a solvent is not particularly limited as long as the solvent does not inhibit the above reaction and can adequately dissolve a part of or all of the compound (II) and the like. The solvent is exemplified by a halogenated hydrocarbon solvent such as dichloromethane and chloroform; an aromatic hydrocarbon solvent such as benzene and toluene; an ether solvent such as diethyl ether and tetrahydrofuran; and an amide solvent such as dimethylformamide and dimethylacetamide.

An iodination reagent to be used is not particularly limited as long as the iodination reagent is generally used for iodination of a benzene ring. For example, molecular iodine, i.e. I$_2$, 1,3-diiodo-5,5'-dimethylhydantoin, i.e. DIH, and N-iodosuccinimide, i.e. NIS, can be used.

An amount of the iodination reagent to be used may be properly adjusted, and is preferably exemplified by not less than 0.9 times by mole and not more than 1.5 times by mole relative to the compound (II). The ratio is more preferably not less than 0.9 times by mole, even more preferably not less than 1.0 time by mole, and more preferably not more than 1.4 times by mole, even more preferably not more than 1.3 times by mole, particularly preferably not more than 1.25 times by mole.

When molecular iodine is used as the iodination reagent, an iodination reaction accelerator is preferably used in combination to accelerate the reaction. As such an iodination reaction accelerator, for example, silver trifluoroacetate and silver acetate can be used.

An amount of the iodination reaction accelerator to be used may be properly adjusted, and is preferably exemplified by not less than 0.5 times by mole and not more than 1.5 times by mole relative to the compound (II). The ratio is more preferably not less than 0.8 times by mole, even more preferably not less than 1.0 time by mole, particularly preferably not less than 1.1 times by mole, and more preferably not more than 1.4 times by mole, even more preferably not more than 1.3 times by mole, particularly preferably not more than 1.25 times by mole.

The above reaction which is characteristic of the present invention method is carried out at −50° C. or lower. In the above reaction, even at −50° C. or lower, the yield is not decreased and an iodine atom can be selectively introduced at the para position of the phenolic hydroxy group of tyrosine.

On the other hand, the lower limit of the reaction temperature is particularly not limited. However, when the temperature is excessively low, the yield may possibly be decreased in some cases. Therefore, the reaction temperature is preferably not less than −100° C. The reaction temperature is more preferably not less than −55° C., even more preferably not more than −60° C., and more preferably not less than −90° C., even more preferably not less than −80° C., particularly preferably not less than −70° C.

For the above reaction, for example, the compound (II) is dispersed or dissolved in a solvent, the temperature of the obtained mixed liquid is adjusted to be −50° C. or lower, and then an iodination reagent is added thereto to be reacted at −50° C. or lower.

The reaction time may be properly adjusted. The reaction may be continued until the presence of the compound (II) cannot be observed by thin-layer chromatography or the like. Alternatively, the reaction time can be determined by a preliminary experiment or the like. For example, the reaction time may be settled to be not less than about 12 hours and not more than about 48 hours.

After the reaction, a general post-treatment may be carried out. For example, the reaction mixture is washed with sodium thiosulfate aqueous solution and the like to decompose unreacted iodine, dried, concentrated under reduced pressure, and the target compound is purified from the obtained residue by chromatography or the like.

As necessary, the iodine atom of the above compound (III) may be transformed to other substituent group to obtain the compound (IV). Such a functional group transformation reaction can be carried out by the person skilled in the art.

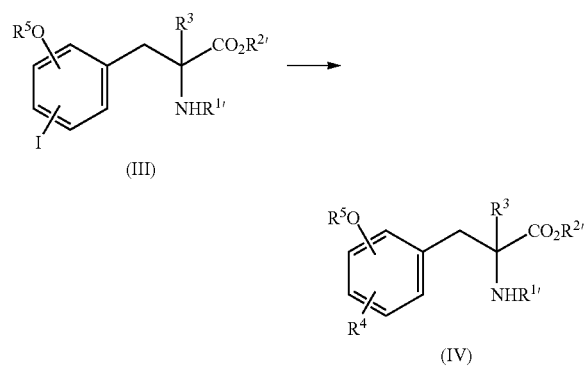

In the above scheme, $R^{1\prime}$, $R^{2\prime}$ and $R^3$ to $R^5$ are the same as the above, and the positions of the iodine atom in the compound (III) and the $R^4$ of the compound (IV) are para to the position of the $R^5O$— group.

As necessary, the phenolic hydroxy group of the compound (III) or the compound (IV) synthesized as the above may be deprotected and then, a substituent group may be introduced thereto. For example, the following reaction may be carried out.

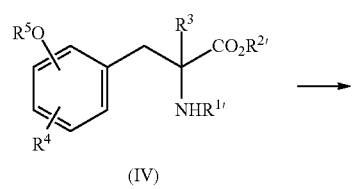

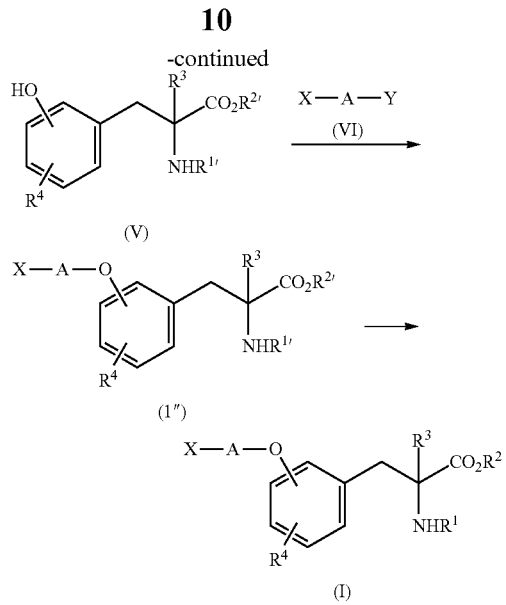

In the above scheme, $R^1$, $R^2$, $R^{1\prime}$, $R^{2\prime}$, $R^3$ to $R^5$, A, X and Y are the same as the above; the position of the $R^4$ of the compound (IV) is para to the position of the $R^5O$— group; the position of the $R^4$ of the compound (V) is para to the position of the hydroxy group; and the position of the $R^4$ of the compound (I″) and the compound (I) is para to the position of the X-A-O— group.

Hereinafter, each of the above steps are described.

5. Deprotection Step at Phenolic Hydroxy Group

In the present step, the phenolic hydroxy group is selectively deprotected. In the reaction, a deprotective condition in which the protective groups of the amino group and the carboxy group are maintained and which is suitable for the kind of the protective group of the phenolic hydroxy group may be applied.

For example, when a silyl ether group is used as the above protective group, tetrabutylammonium fluoride (TBAF), hydrofluoric acid (HF), cesium fluoride (CsF), potassium fluoride (KF) and the like, which can utilize a strong affinity between silicon and fluorine, can be used.

As a detail reaction condition such as a solvent and temperature of the present step, an ordinary condition which is well-known to the person skilled in the art may be applied similarly to the case of the protective group of the amino group.

6. Alkylation Step of Phenolic Hydroxy Group

Then, for example, the tyrosine derivative (I″) can be synthesized by reacting the phenolic hydroxy group of the compound (V), which is obtained by removing the protective group of the phenolic hydroxy group, with the compound (VI).

In the present invention, the term "leaving group" is a group which is eliminated by the attack of a nucleophilic agent in a nucleophilic substitution reaction, and is exemplified by a group which can form an ether bond with the phenolic hydroxy group. Such a leaving group to be used is exemplified by a halogen atom leaving group which has a leaving ability, such as a chlorine atom, a bromine atom and an iodine atom; a sulfonyloxy group such as a methanesulfonyloxy group, a trifluoromethanesulfonyloxy group, a chloromethanesulfonyloxy group, an ethanesulfonyloxy group, a benzenesulfonyloxy group and a toluenesulfonyloxy group. Two leaving groups of the compound (VI), i.e. "X" and "Y", may be the same or different from each other. When two leaving groups are different from each other, a leaving group of which reactivity to the phenolic hydroxy group is higher is selected as "Y" more than that of "X".

Any one end of "A", i.e. —(CH$_2$)$_l$—[Z(CH$_2$)$_m$]$_n$—, in the compound (VI) and the like may be bound to the "X" or the oxygen atom in the phenolic hydroxy group. For example, the structure of the compound (VI) may be any one of X—(CH$_2$)$_l$—[Z(CH$_2$)$_m$]$_n$—Y and Y—(CH$_2$)$_l$—[Z(CH$_2$)$_m$]$_n$—X. In addition, the structure of X-A-O-Ph, wherein Ph is a benzene ring, in the compound (I), the compound (I') and the compound (I'') may be any one of X—(CH$_2$)$_l$—[Z (CH$_2$)$_m$]$_n$—O-Ph and X—[(CH$_2$)$_m$—Z]$_n$—(CH$_2$)$_l$—O-Ph. It is preferred that the compound (VI), the compound (I), the compound (I') and the compound (I'') have a structure of —O—(CH$_2$)$_l$—[Z(CH$_2$)$_m$]$_n$—X.

It is preferred that the above reaction is carried out in a solvent in the presence of a base. The solvent to be used is exemplified by an alcohol solvent such as methanol and ethanol; an ether solvent such as diethyl ether and tetrahydrofuran; an amide solvent such as dimethylformamide and dimethylacetamide.

As the above base, an organic amine such as triethylamine, diethylaminoethanol and pyridine; a hydroxide of an alkali metal, such as sodium hydroxide and potassium hydroxide; a hydrogencarbonate of an alkali metal, such as sodium hydrogencarbonate and potassium hydrogencarbonate; a carbonate of an alkali metal, such as sodium carbonate and potassium carbonate can be used.

When the "Y" is a hydroxy group, the hydroxy group may be selectively reacted with the phenolic hydroxy group in the presence of triphenylphosphine and diethyl azodicarboxylate to obtain a phenol ether.

Finally, as necessary, the amino group and/or the carboxy group of the compound (I'') may be deprotected.

The tyrosine derivative of the present invention is characterized in being represented by the following formula (I).

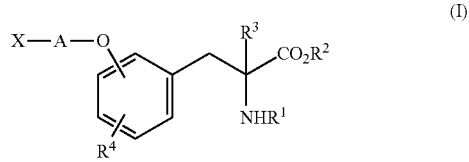

(I)

wherein $R^1$ is a hydrogen atom or a protective group for the amino group;

$R^2$ is a hydrogen atom or a protective group for the carboxy group;

$R^3$ is a hydrogen atom or a C$_{1-6}$ alkyl group;

$R^4$ is a halogen atom, a hydroxy group, a C$_{1-6}$ alkyl group, a C$_{1-6}$ halogenated alkyl group, an amino group, a mono(C$_{1-6}$ alkyl) amino group, a di(C$_{1-6}$ alkyl) amino group, an aryl group optionally having substituent α, a heterocyclic group optionally having substituent α, a C$_{1-6}$ alkoxy group, a C$_{1-6}$ alkylthio group, a C$_{1-6}$ halogenated alkoxy group or a C$_{7-13}$ aralkyloxy group optionally having substituent α;

A is —(CH$_2$)$_l$—[Z(CH$_2$)$_m$]$_n$— wherein Z is an amino group, an ether group, a thioether group, a carbonyl group, a thionyl group, an ester group, an amide group, a urea group or a thiourea group; l is an integer of not less than 1 and not more than 6; m is an integer of not less than 1 and not more than 4; n is an integer of not less than 0 and not more than 4;

X is a leaving group selected from the group consisting of a chlorine atom, a bromine atom, an iodine atom, a methanesulfonyloxy group, a trifluoromethanesulfonyloxy group, a chloromethanesulfonyloxy group, an ethanesulfonyloxy group, a benzenesulfonyloxy group and a toluenesulfonyloxy group;

substituent α is one or more substituents selected from the group consisting of a halogen atom, a hydroxy group, a cyano group, a thiol group, an amino group, a mono(C$_{1-6}$ alkyl) amino group, a di(C$_{1-6}$ alkyl) amino group, a C$_{1-6}$ alkyl group, a C$_{1-6}$ alkoxy group, a C$_{1-6}$ halogenated alkyl group and a C$_{1-6}$ alkylthio group;

provided that the position of R$^4$ is para to the position of the X-A-O— group.

In the present invention, the term "halogen atom" is a fluorine atom, chlorine atom, a bromine atom, an iodine atom, preferably a chlorine atom, a bromine atom, an iodine atom.

The term "C$_{1-6}$ alkyl group" is a linear, branched or cyclic saturated aliphatic hydrocarbon group of which carbon number is not less than 1 and not more than 6. The group is exemplified by a methyl group, an ethyl group, a n-propyl group, an isopropyl group, a n-butyl group, an isobutyl group, a t-butyl group, a n-pentyl group, a n-hexyl group, a cyclopropyl group, a cyclobutyl group, a cyclopentyl group and a cyclohexyl group. The group is preferably a C$_{1-4}$ alkyl group, more preferably a C$_{1-2}$ alkyl group, and most preferably a methyl group.

The term "C$_{1-6}$ halogenated alkyl group" is a C$_{1-6}$ alkyl group which is substituted by at least one halogen atom. The group is exemplified by a chloromethyl group, a bromomethyl group, a trifluoromethyl group and a pentafluoroethyl group. The group is preferably a C$_{1-4}$ halogenated alkyl group, and more preferably C$_{1-2}$ halogenated alkyl group.

The term "mono(C$_{1-6}$ alkyl)amino group" is an amino group which is substituted by one C$_{1-6}$ alkyl group. The group is exemplified by a methylamino group, an ethylamino group, an isopropylamino group, a t-butylamino group, a n-pentylamino group and a n-hexylamino group.

The term "di(C$_{1-6}$ alkylamino group" is an amino group which is substituted by two C$_{1-6}$ alkyl groups. The C$_{1-6}$ alkyl groups may be the same or different from each other. The group is exemplified by a dimethylamino group, a diethylamine group, a diisopropylamino group, a t-butylmethylamino group, a t-butylethylamino group, a di(t-butyl)amino group, a di(n-pentyl)amino group and a di(n-hexyl)amino group.

The term "C$_{6-12}$ aryl group" is an aromatic hydrocarbon group of which carbon number is not less than 6 and not more than 12. The group is exemplified by a phenyl group, an indenyl group, a naphthyl group and a biphenyl group, and is preferably a phenyl group.

The term "heterocyclic group" is a five-membered, six-membered or condensed saturated heterocyclic group or a five-membered, six-membered or condensed heteroaryl group which have at least one hetero atom such as a nitrogen atom, an oxygen atom and a sulfur atom. The "heterocyclic group" is exemplified by a five-membered saturated heterocyclic group such as a pyrrolidinyl group, an imidazolidinyl group, a pyrazolidinyl group, a tetrahydrothiophenyl group, a tetrahydrofuranyl group, an oxazolidinyl group, an isoxazolidinyl group, a thiazolidinyl group and an isothiazolidinyl group; and a six-membered saturated heterocyclic group such as a piperidinyl group, a piperazinyl group, a morpholinyl group and a thiomorpholinyl group. The "heteroaryl group" is exemplified by a five-membered heteroaryl group such as a pyrrolyl group, an imidazolyl group, a pyrazolyl group, a tetrazolyl group, a thienyl group, a furyl group, an oxazolyl group, an isoxazolyl group, a thiazolyl group and an isothiazolyl group; a six-membered heteroaryl group such as pyridyl group, a pyrazinyl group, a pyrimidinyl group and a pyridazinyl group; and a condensed heteroaryl group such as an indolyl group, an isoindolyl group, an isoindole-1,3-dione-2-yl group, a quinolyl group, an isoquinolyl group, a benzofuranyl group, a chromenyl group, a benzothienyl group and a tetrahydroimidazol[1,2-a]pyrazine group.

The term "$C_{1-6}$ alkoxy group" is a linear, branched or cyclic aliphatic hydrocarbonoxy group of which carbon number is not less than 1 and not more than 6. The group is exemplified by a methoxy group, an ethoxy group, a propoxy group, an isopropoxy group, a butoxy group, an isobutoxy group, a t-butoxy group, a pentoxy group, a hexoxy group, a cyclopropyloxy group, a cyclobutyloxy group, a cyclopentyloxy group and a cyclohexyloxy group. The group is preferably a $C_{1-4}$ alkoxy group, and more preferably a $C_{1-2}$ alkoxy group.

The term "$C_{1-6}$ alkylthio group" is a linear, branched or cyclic aliphatic hydrocarbonthio group of which carbon number is not less than 1 and not more than 6. The group is exemplified by a methylthio group, an ethylthio group, a propylthio group, an isopropylthio group, a butylthio group, an isobutylthio group, a t-butylthio group, a pentylthio group, a hexylthio group, a cyclopropylthio group, a cyclobutylthio group, a cyclopentylthio group and a cyclohexylthio group. The group is preferably a $C_{1-4}$ alkylthio group, more preferably a $C_{1-2}$ alkylthio group, and most preferably a methylthio group.

The term "$C_{1-6}$ halogenated alkoxy group" is a $C_{1-6}$ halogenated alkyloxy group. The group is exemplified by a chloromethyloxy group, a bromomethyloxy group, a trifluoromethyloxy group and a pentafluoroethyloxy group. The group is preferably a $C_{1-4}$ halogenated alkoxy group, and more preferably a $C_{1-2}$ halogenated alkoxy group.

The term "$C_{7-13}$ aralkyloxy group" is an alkyl group which is substituted by one aryl group and of which carbon number is not less than 7 and not more than 13. The group is exemplified by a benzyl group, a phenacyl group, a naphthylmethyl group and a biphenylmethyl group, and is preferably a benzyl group.

The number of substituent α in a $C_{6-12}$ aryl group, a heterocyclic group and a $C_{7-13}$ aralkyloxy group is particularly not limited, and is preferably not less than 1 and not more than 5. The number is more preferably not more than 3 and even more: preferably not more than 2. When the number of substituent α is 2 or more, the substituents may be the same or different from each other. When a $C_{7-13}$ aralkyloxy group has substituent α, the substituent exists on the aryl group. The carbon number of substituent α is not included in the carbon number of a $C_{6-12}$ aryl group and a $C_{7-13}$ aralkyloxy group.

As a tyrosine derivative, there are a L-tyrosine derivative and a D-tyrosine derivative, both of which are included in the range of the present invention. According to a purpose, a L-tyrosine derivative, a D-tyrosine derivative or the mixture thereof, such as racemate, may be properly selected. In general, a racemate consists of L body and D body in a ratio of 1:1. In general, a L-tyrosine derivative, which is a derivative of a natural amino acid, has highest utilization value.

The tyrosine derivative (I) of the present invention may be a salt. Such a salt is exemplified by an inorganic acid salt such as a hydrochloride, a hydrobromide, a hydroiodide, a nitrate, a sulfate and a phosphate; an organic acid salt such as an oxalate, a malonate, a maleate, a fumarate, a lactate, a malate, a citrate, a tartrate, a benzoate, a trifluoroacetate, an acetate, a methanesulfonate, a p-toluenesulfonate and a trifluoromethanesulfonate; an alkali metal salt such as a sodium salt and a potassium salt; an alkaline earth metal salt such as a calcium salt and a magnesium salt; an ammonium salt; an amino acid salt such as an aspartate, a glutamate, a lysine salt, an alginate and a histidine salt.

The tyrosine derivative (I) of the present invention can be produced by the above-described present invention method.

Alternatively, the present invention method may be properly modified by a method which is known to the person skilled in the art to produce the tyrosine derivative (I) of the present invention.

For example, o-tyrosine may be used as a raw material compound other than m-tyrosine, the position of an iodine atom to be introduced may be determined by adjusting a reaction temperature in the iodination reaction, and further the introduced iodine atom may be transformed to other functional group if necessary.

The tyrosine derivative (I) of the present invention has an actively reactive group in the substituent group at the phenolic hydroxy group and on the benzene ring, and therefore the tyrosine derivative is useful as a synthetic intermediate. In addition, for example, the tyrosine derivative itself can be used as a non-naturally occurring amino acid for improving or modifying an activity of an enzyme such as t-PA by replacing a part of amino acids which constitutes the enzyme by the tyrosine derivative. Furthermore, the tyrosine derivative can be used as a diagnostic agent and a bioimaging agent which utilizes in vivo redox reaction, a nitroxyl radical or the like. In particular, the tyrosine derivative of the present invention exhibits antagonism against a melatonin $MT_1$ receptor and is useful as a melatonin $MT_1$ receptor antagonist. Therefore, the tyrosine derivative of the present invention can be utilized as antidepressant agent or the like.

The tyrosine derivative of the present invention can be used for treating depression or the like as a medicinal preparation containing the derivative as an active component and a pharmaceutically acceptable organic or inorganic solid or liquid excipient which is suitable for oral administration or parenteral administration. Such a medicinal preparation can be developed in a form of an encapsulated formulation, a tablet, a sugar-coated tablet, a granule, an inhalant, a suppository, a solution, a lotion, a dispersion, an emulsion or the like. As necessary, a general additive agent, such as an auxiliary agent, a stabilizing agent, a wetting agent, an emulsifier and a buffering agent, can be added to the medicinal preparation.

A dosage amount of the tyrosine derivative according to the present invention for a treatment is dependent on a severity, age, sex, condition or the like of a patient, and for example, a dosage amount of not less than about 0.01 mg/kg and not more than about 50 mg/kg on a basis of a patient's weight may be effective.

EXAMPLES

Hereinafter, the present invention is described in more detail with Examples. However, the present invention is not limited by the following Examples, and the present invention can be appropriately modified to be carried out within a range which adapts to the contents of this specification. Such a modified embodiment is also included in the range of the present invention.

Example 1

Production of Iodinated Tyrosine Derivative

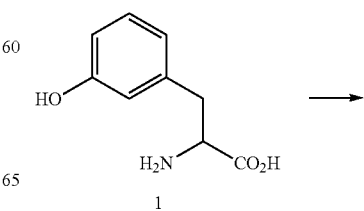

1

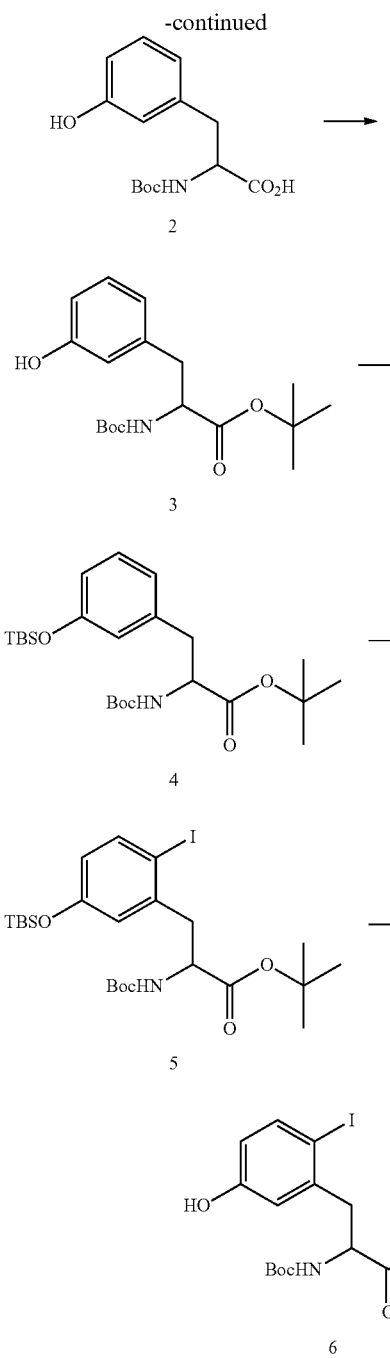

(1) Protection of Amino Group to Synthesize Compound 2

To a mixed solution obtained by dissolving D/L-m-tyrosine (Compound 1, 3.0 g, 27.6 mmol) and triethylamine (4.19 g, 41.4 mmol) in a mixed solvent of dioxane/water=1/1, di-t-butyl pyrocarbonate (6.62 g, 30.4 mmol) was slowly added at 0° C. The mixture was stirred at −2° C. overnight. The reaction mixture was concentrated under reduced pressure, and sodium hydrogencarbonate solution was added thereto. After the aqueous layer was washed with ethyl acetate and neutralized by adding hydrochloric acid, extraction was carried out with ethyl acetate. The obtained organic layers were combined. The organic layer was washed with saturated saline and dried over anhydrous sodium sulfate. The solid components were removed by filtration and the filtrate was concentrated under reduced pressure, to obtain colorless powder (amount: 7.5 g, yield: 97%).

$^1$H-NMR (400 MHz, CD$_3$OD, TMS) δ7.08 (t, J=7.79 Hz, 1H), 6.66 (m, 3H), 4.31 (m, 1H), 3.05 (m, 1H), 2.84 (m, 1H), 1.39 (s, 9H)

(2) Protection of Carboxy Group to Synthesize Compound 3

The N-protected tyrosine (Compound 2, 7.5 g, 26.7 mmol) obtained in the above (1) was dissolved in toluene (133 mL), and t-butyl alcohol (35 mL) was further added thereto. After the obtained reaction mixture was heated to reflux, N,N-dimethylformamide dineopentyl acetal (18.5 g, 21.7 mmol) was added dropwise thereto over 55 minutes. After the mixture was heated to reflux for 3 hours, the mixture was cooled to room temperature and saturated sodium hydrogencarbonate solution was added thereto. The target compound was extracted from the aqueous layer with dichloromethane two times, and the obtained organic layer was dried over anhydrous sodium sulfate. The solid components were removed by filtration, and the filtrate was concentrated under reduced pressure. The protected tyrosine as colorless powder was purified from the residue by silica gel column chromatography (amount: 7.06 g, yield: 78%).

$^1$H-NMR (400 MHz, CDCl$_3$, TMS) δ7.14 (t, J=7.79 Hz, 1H), 6.70 (m, 3H), 5.26 (s, 1H), 5.01 (m, 1H), 4.42 (m, 1H), 2.99 (m, 2H), 1.42 (s, 9H), 1.40 (s, 9H)

(3) Protection of Phenolic Hydroxy Group to Synthesize Compound 4

To a DMF (36 mL) solution of TBSCl (3.23 g, 21.4 mmol), the protected tyrosine (Compound 3, 6.03 g, 17.9 mmol) obtained in the above (2) and imidazole (3.04 g, 44.6 mmol) was added at 0° C. The mixture was heated to room temperature. After 2 hours, the reaction mixture was diluted with water and extraction was carried out with ethyl acetate. The extract was washed with water and saturated saline, and then dried over anhydrous sodium sulfate. After filtration, the filtrate was concentrated under reduced pressure. Compound 4 of which phenolic hydroxy group was protected was obtained by purifying from the residue with silica gel column chromatography (amount: 7.66 g, yield: 95%).

$^1$H-NMR (400 MHz, CDCl$_3$, TMS) δ7.12 (t, J=7.79 Hz, 1H), 6.75 (d, J=7.79 Hz, 1H), 6.70 (d, J=7.79 Hz, 1H), 6.65 (s, 1H), 4.95 (m, 1H), 4.43 (m, 1H), 3.00 (d, J=5.95 Hz, 1H), 1.42 (s, 9H), 1.41 (s, 9H), 0.97 (s, 9H)

(4) Iodination to Synthesize Compound 5

Compound 4 (8.31 g, 18.4 mmol) obtained in the above (3) and CF$_3$CO$_2$Ag (4.68 g, 21.2 mmol) were added to chloroform (180 mL) to obtain a dispersion, and iodine (5.14 g, 20.2 mmol) was added to the dispersion at −65° C. The mixture was stirred at −65° C. overnight. The reaction mixture was filtered. The filtrate was diluted with ethyl acetate, and washed with sodium thiosulfate aqueous solution and saturated saline. The organic layer was dried over anhydrous magnesium sulfate. After filtration, the filtrate was concentrated under reduced pressure. A mixture of Compound 4 as raw material compound and Compound 5 as the target compound was obtained as colorless powder by purifying from the residue with silica gel column chromatography (amount: 8.79 g).

$^1$H-NMR (400 MHz, CDCl$_3$, TMS) δ7.62 (d, J=8.24 Hz, 1H), 6.73 (s, 1H), 6.46 (d, J=8.24 Hz, 1H), 5.00 (d, J=8.24 Hz, 1H), 4.48 (m, 1H), 3.17 (m, 1H), 2.96 (m, 1H), 1.42 (s, 9H), 1.39 (s, 9H), 0.96 (s, 9H)

(5) Deprotection of Phenolic Hydroxy Group to Synthesize Compound 6

Compound 5 (1.33 g, 2.30 mmol) obtained in the above (4) was dissolved in THF (8 mL). To the solution, TBAF (3.5 mL, 1M THF solution) was added at 0° C. The mixture was stirred for 1 hour. Then, water was added thereto, and extraction was carried out with ethyl acetate two times. The organic layers were combined. The combined organic layer was washed with saturated saline and dried over anhydrous sodium sulfate. After filtration, the filtrate was concentrated under reduced pressure to obtain Compound 6 as the target compound (amount: 1.03 g, yield: 96%).

$^1$H-NMR (400 MHz, CDCl$_3$, TMS) δ7.63 (d, J=8.24 Hz, 1H), 6.80 (s, 1H), 6.49 (d, J=8.70 Hz, 1H), 5.86 (s, 1H), 5.08 (m, 1H), 4.52 (m, 1H), 2.99 (m, 1H), 1.43 (s, 9H), 1.39 (s, 9H)

Example 2

Introduction of Substituent Group to Phenolic Hydroxy Group

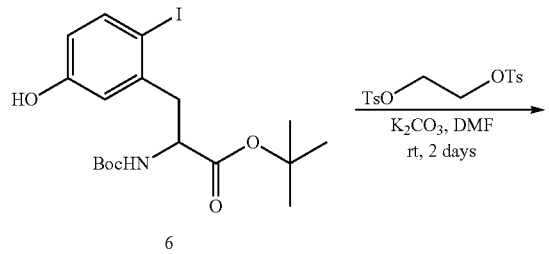

To an anhydrous DMF (2.5 mL) solution of Compound 6 (0.12 g, 0.25 mmol) obtained in the above Example 1(5) and potassium carbonate (0.10 g, 0.75 mmol), ethyleneglycol bis(p-toluenesulfonate) (0.19 g, 0.5 mmol) was added. After the mixture was stirred at room temperature for 2 days, the mixture was diluted with water and extraction was carried out with ethyl acetate (about 20 mL) three times. The combined organic layer was washed with water and saturated saline, and dried over magnesium sulfate. After filtration, the filtrate was concentrated. Compound 7 was obtained by purifying from the residue with silica gel column chromatography (0.53 g, 54%).

$^1$H-NMR (400 MHz, CDCl$_3$, TMS) δ7.81 (dt, 0.4 Hz and 1.9 Hz, 2H), 7.65 (d, J=8.7 Hz, 1H), 7.36 (d, J=7.8 Hz, 2H), 6.72 (s, 1H), 6.43 (dd, J=8.7 Hz and 1.8 Hz, 1H), 5.02 (m, 1H), 4.5 (m, 1H), 4.35 (m, 2H), 4.11 (m, 2H), 3.17 (dd, J=14.0 Hz and 5.7 Hz, 1H), 2.98 (m, 1H), 2.47 (s, 3H), 1.43 (s, 9H), 1.38 (s, 9H)

Example 3

Examination for Reaction Temperature of Iodination Reaction

Compound 5 was synthesized similarly to the above Example 1 (4) except that a molar ratio of the iodination reagent: CF$_3$CO$_2$Ag—I$_2$ relative to Compound 4, reaction temperature and reaction time were changed as Table 1. After purification with silica gel column chromatography, the obtained compounds were analyzed with $^1$H-NMR and yields of Compound 5 as the target compound, in which an iodine atom was introduced at the para position of TBSO— group, Compound 5' as a by-product, in which an iodine atom was introduced at the ortho position of TBSO— group, i.e. at the para position of the benzyl position, and unreacted Compound 4 from the peak area of the obtained charts. In Table 1, "main" represents non-quantitative production quantity since the target peak was overlapped with other peak of by-product so that yield could not calculated, and "trace" represents the case where the yield calculated from NMR data was less than 1%.

TABLE 1

| Run | Amount of iodination reagent | Reaction temperature | Reaction time (h) | Yield (%) Compound 5 | Compound 5' | Compound 4 | Ratio of Compound 5/ Compound 5' |
|---|---|---|---|---|---|---|---|
| 1 | 1.00 eq | rt | 3 | 85% | 6% | 3% | 14 |
| 2 | 1.00 eq | 2° C. (ice bath) | 47 | 83% | 5% | 4% | 17 |
| 3 | 1.25 eq | 2° C. (ice bath) | 5 | main | trace | 0% | — |
| 4 | 1.00 eq | −40° C. | 117 | 87% | 3% | 2% | 29 |
| 5 | 1.00 eq | −60° C. | 168 | 85% | 2% | 8% | 43 |
| 6 | 1.25 eq | −60° C. | 114 | 91% | 2% | trace | 46 |

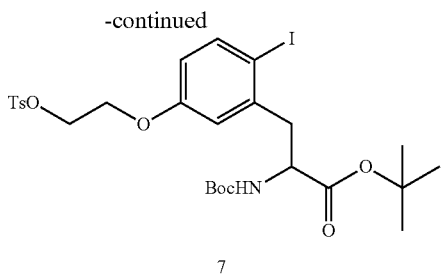

As the results demonstrated in Table 1, when the reaction temperature was −40° C. or higher, the ratio of Compound 5 as the target compound relative to Compound 5' as a by-product was about 30 at the most. Hereinafter, the ratio is abbreviated to "Compound 5/Compound 5' ratio". The physical properties of Compound 5 and Compound 5' are similar to each other, and it is very difficult to separate one from the other. Therefore, it is preferred that the value of Compound 5/Compound 5' ratio is large as much as possible. In addition, when the reaction temperature was 2° C. and an amount of an iodination reagent to be used relative to Compound 4 was increased to accelerate the reaction, an amount of by-product other than Compound 5' was increased. Such a by-product other than Compound 5' is supposed to be a diiodo compound or a triiodo compound.

On the other hand, when the reaction temperature was adjusted to be −60° C., Compound 5/Compound 5' ratio was increased to about 40, and the yield of Compound 5 was about 90% whereas the yield of Compound 5' was merely 2%. In addition, even when an amount of an iodination reagent to be used was increased, an amount of by-product to be produced other than Compound 5' was suppressed.

It was clarified from the above results that the reaction temperature of an iodination reaction should be adjusted to −50° C. or lower in order to effectively and selectively iodinate the para position of the phenolic hydroxy group or the protected phenolic hydroxy group of a tyrosine derivative.

Example 4

Iodination

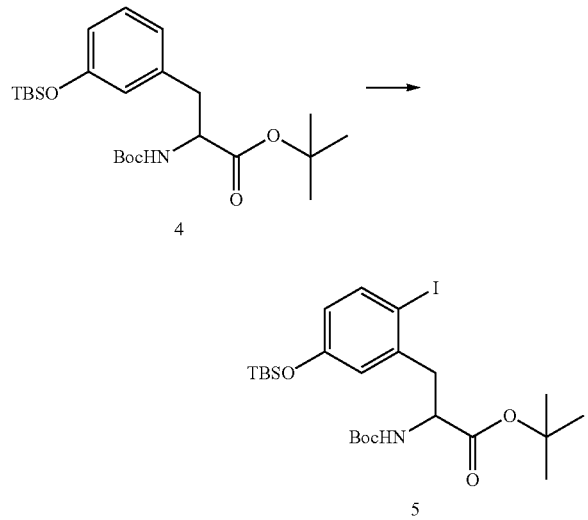

Compound 4 (452 mg, 1.0 mmol) obtained in the above Example 1(3) and CF$_3$CO$_2$Ag (276 mg, 1.25 mmol) were added to chloroform (10 mL) to obtain a dispersion. Iodine (317 mg, 1.25 mmol) was added to the dispersion at −60° C., and the mixture was stirred at −60° C. for 5 days. After the reaction mixture was filtrated and the filtrate was diluted with ethyl acetate, the diluted mixture was washed with sodium thiosulfate aqueous solution and saturated saline. The organic layer was dried over anhydrous magnesium sulfate. After filtration, the filtrate was concentrated under reduced pressure. A mixture of Compound 5 as the target compound and Compound 5' as a by-product was obtained as colorless powder by purifying from the residue with silica gel column chromatography (Compound 5: 528 mg, yield: 91%, Compound 5': 14 mg, yield: 2% (the yields were calculated from NMR)).

Compound 5

$^1$H-NMR (400 MHz, CDCl$_3$, TMS) δ7.62 (d, J=8.24 Hz, 1H), 6.73 (s, 1H), 6.46 (d, J=8.24 Hz, 1H), 5.00 (d, J=8.24 Hz, 1H), 4.48 (m, 1H), 3.17 (m, 1H), 2.96 (m, 1H), 1.42 (s, 9H), 1.39 (s, 9H), 0.96 (s, 9H), 0.18 (s, 6H)

Compound 5'

$^1$H-NMR (400 MHz, CDCl$_3$, TMS) δ7.63 (d, J=7.76 Hz, 1H), 6.65 (s, 1H), 6.50 (dd, J=8.22 Hz and 1.83 Hz, 1H), 4.97 (d, J=7.77 Hz, 1H), 4.43 (m, 1H), 2.97 (m, 2H), 1.42 (s, 9H), 1.41 (s, 9H), 1.06 (s, 9H), 0.28 (s, 6H)

Example 5

O-Alkylation

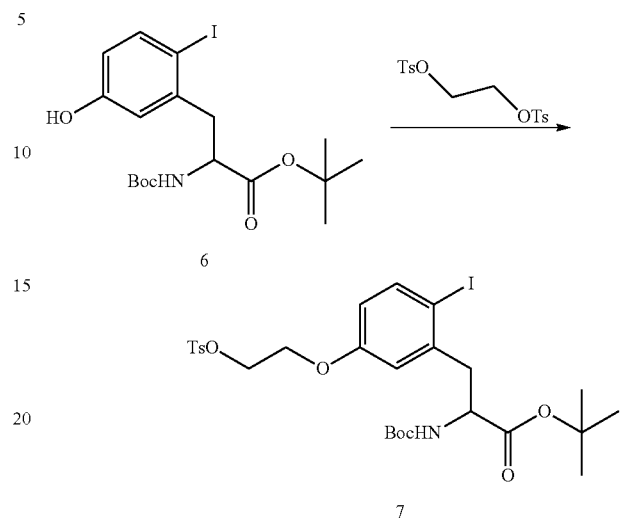

Compound 6 (1.6 g, 3.4 mmol) obtained in the above Example 1(5), potassium carbonate (2.5 g, 18.1 mol) and ethyleneglycol bis(p-toluenesulfonate) (4.0 g, 10.8 mmol) were dissolved in anhydrous acetone (30 mL). The obtained solution was heated to reflux for 21 hours. After the reaction mixture was cooled, the mixture was diluted with water and extraction was carried out with ethyl acetate (about 20 mL) three times. The combined organic layers was washed with water and saturated saline, and dried over anhydrous sodium sulfate. After filtration, the filtrate was concentrated. Compound 7 was obtained by purifying from the residue with silica gel column chromatography (1.48 g, 59%). $^1$H-NMR (400 MHz, CDCl$_3$, TMS) δ7.81 (dt, J=8.4 Hz and 1.9 Hz, 2H), 7.65 (d, J=8.7 Hz, 1H), 7.36 (d, 3=7.8, 2H), 6.72 (s, 1H), 6.43 (dd, J=8.7 Hz and 1.8 Hz, 1H), 5.02 (m, 1H), 4.5 (m, 1H), 4.35 (m, 2H), 4.11 (m, 2H), 3.17 (dd, J=14.0 Hz and 5.7 Hz, 1H), 2.98 (m, 1H), 2.47 (s, 3H), 1.43 (s, 9H), 1.38 (s, 9H)

Example 6

O-Alkylation

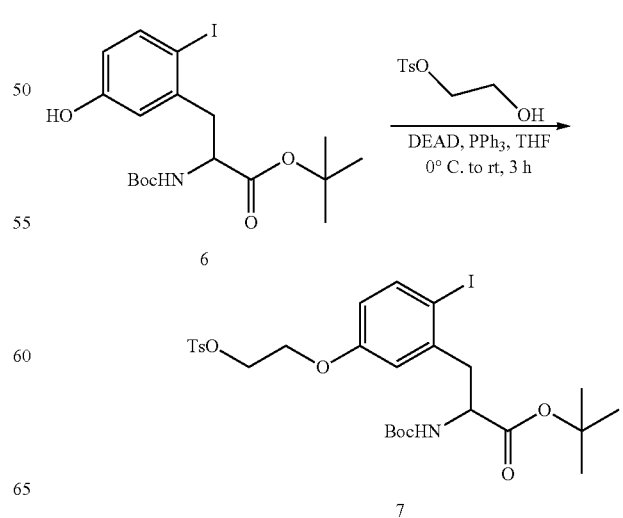

Compound 6 (116 mg, 0.25 mmol) obtained in the above Example 1(5), triphenylphosphine (131 mg, 0.5 mmol) and 2-hydroxyethyl-4-methyl benzenesulfonate (108 mg, 0.5 mmol) were dissolved in anhydrous THF (2.5 mL). The solution was cooled with ice, and then diethyl azodicarboxylate (218 mg, 0.5 mmol) was added thereto. The temperature of the reaction mixture was increased to room temperature and stirred for 3 hours. Then, the reaction mixture was diluted with water, and extraction was carried out with ethyl acetate. The organic layer was washed with water and saturated saline, and dried over anhydrous magnesium sulfate. After filtration, the filtrate was concentrated under reduced pressure. Compound 7 was obtained by purifying from the residue with silica gel column chromatography (amount: 112 mg, yield: 68%).

Example 7

O-Alkylation

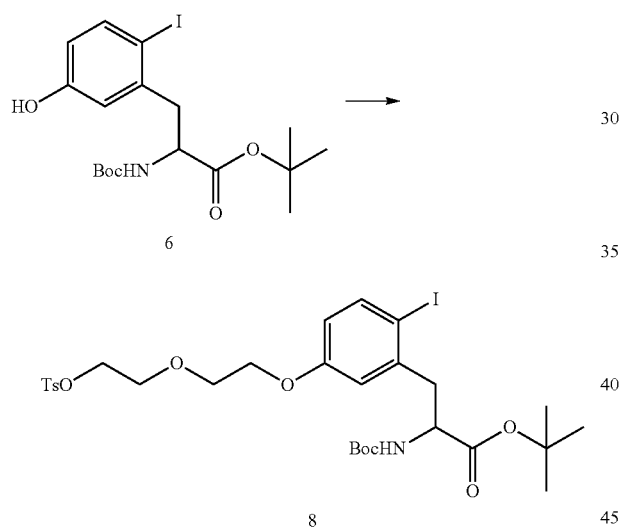

Compound 6 (0.6 g, 1.3 mmol) obtained in the above Example 1 (5), potassium carbonate (0.9 g, 10 mmol) and di-ethyleneglycol bis(p-toluenesulfonate) (1.61 g, 3.9 mmol) were dissolved in anhydrous DMF (10 mL). After the solution was stirred at room temperature for 5 days, the solution was diluted with water and extraction was carried out with ethyl acetate (about 20 mL) three times. The combined organic layers was washed with water and saturated saline, and dried over anhydrous sodium sulfate. After filtration, the filtrate was concentrated. Compound 8 was obtained by purifying from the residue with silica gel column chromatography (0.61 g, 67%).

$^1$H-NMR (400 MHz, CDCl$_3$, TMS) δ7.80 (dt, J=8.5 Hz and 1.9 Hz, 2H), 7.67 (d, 0.3=8.7 Hz, 1H), 7.32 (d, J=8.2 Hz, 2H), 6.81 (s, 1H), 6.53 (dd, J=8.5 Hz and 2.5 Hz, 1H), 5.09 (m, 1H), 4.5 (m, 1H), 4.19 (m, 2H), 4.01 (m, 2H), 3.76 (m, 4H), 3.19 (dd, J=14.0 Hz and 5.7 Hz, 1H), 2.98 (m, 1H), 2.44 (s, 3H), 1.43 (s, 9H) 1.38 (s, 9H)

Example 8

O-Alkylation

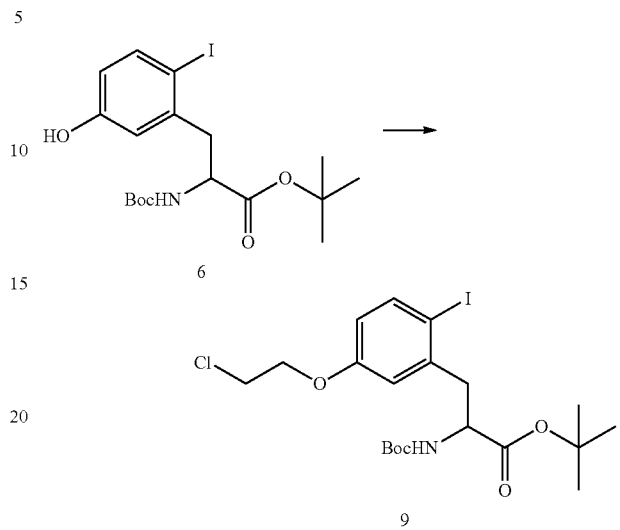

To a THF (2 mL) solution of Compound 6 (0.35 g, 0.76 mmol) obtained in the above Example 1(5) and triphenylphosphine (396 mg, 1.5 mmol), 2-chloroethanol (100 μL, 1.5 mmol) was added. The mixture was cooled with ice. Diethyl azodicarboxylate (690 μL, 1.5 mmol) was slowly added thereto. After addition, the mixture was stirred at room temperature. After the reaction, the mixture was concentrated. Compound 9 was obtained by purifying from the residue with silica gel chromatography (0.31 g, 77%).

$^1$H-NMR (400 MHz, CDCl$_3$, TMS) δ7.70 (d, J=8.7 Hz, 1H), 6.84 (s, 1H), 6.56 (dd, J=8.7 Hz and 1.8 Hz, 1H), 5.04 (m, 1H), 4.5 (m, 1H), 4.19 (t, J=5.7 Hz, 2H), 3.79 (t, J=5.7 Hz, 2H), 3.21 (dd, J=13.7 Hz and 5.5 Hz, 1H), 2.99 (m, 1H), 1.44 (s, 9H), 1.39 (s, 9H)

Example 9

O-Alkylation

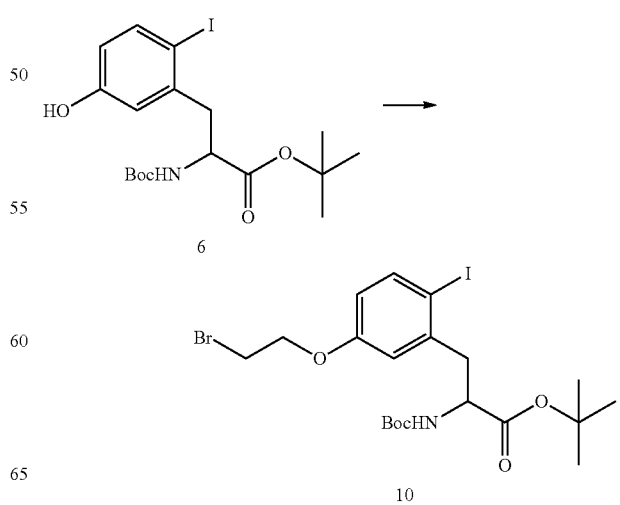

Compound 6 (0.35 g, 0.76 mmol) obtained in the above Example 1(5) and triphenylphosphine (254 mg, 0.97 mmol) were dissolved in THF (2 mL). To the solution, 2-bromoethanol (70 μL, 0.97 mmol) was added. The mixture was cooled with ice. Diethyl azodicarboxylate (440 μL, 0.97 mmol) was slowly added thereto. After addition, the mixture was stirred at room temperature. After the reaction, the mixture was concentrated. Compound 10 was obtained by purifying from the residue with silica gel chromatography (0.21 g, 57%).

$^1$H-NMR (400 MHz, CDCl$_3$, TMS) δ7.70 (d, J=8.7 Hz, 1H), 6.83 (s, 1H), 6.56 (t, J=4.3 Hz, 1H), 5.04 (m, 1H), 4.5 (m, 1H), 4.25 (t, J=6.2 Hz, 2H), 3.62 (t, J=6.2 Hz, 2H), 3.20 (dd, J=14.0 Hz and 5.7 Hz, 1H), 3.00 (m, 1H), 1.44 (s, 9H), 1.39 (s, 9H)

Example 10

Synthesis of Optically-Active Compound

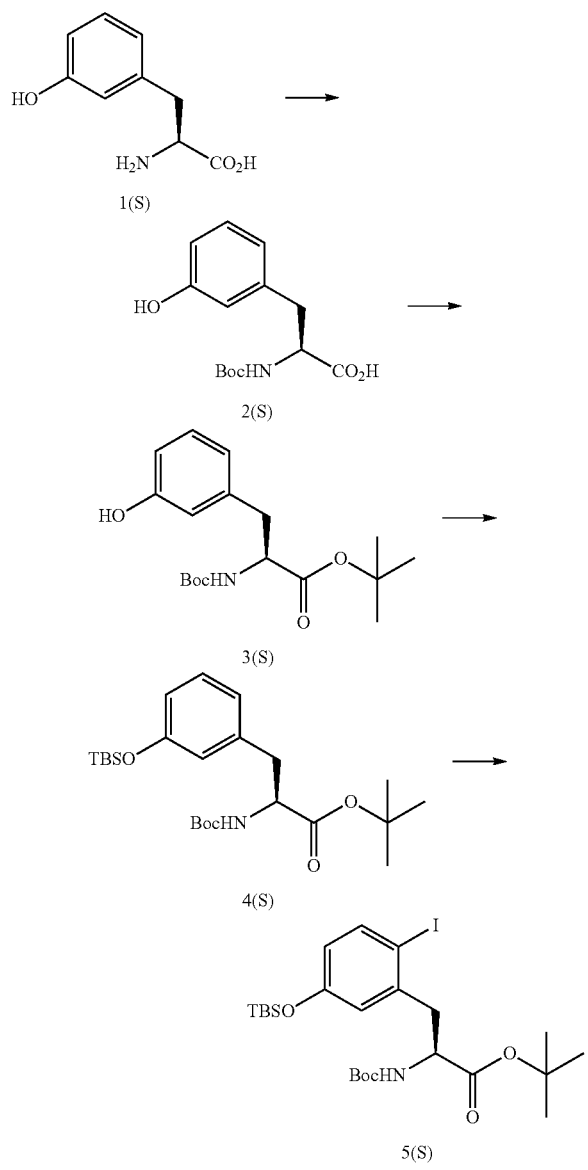

An optically-active compound 5(s) (99.8% ee) was synthesized similarly to the synthesis route described in the above Example 1 except that an optically-active L-m-tyrosine was used instead of DL-m-tyrosine as a raw material compound.

HPLC retention time: 11.46 min

Column: CHIRALPAC IA 4.6 mmφ×250 mm, manufactured by Daicel Corporation

Flow speed: 0.8 mL/min

Column oven temperature: 25° C.

Detection light wave-length: 233 nm

Eluent: hexane/ethanol=99/1

Example 11

Optical Resolution of Racemic Compound 5

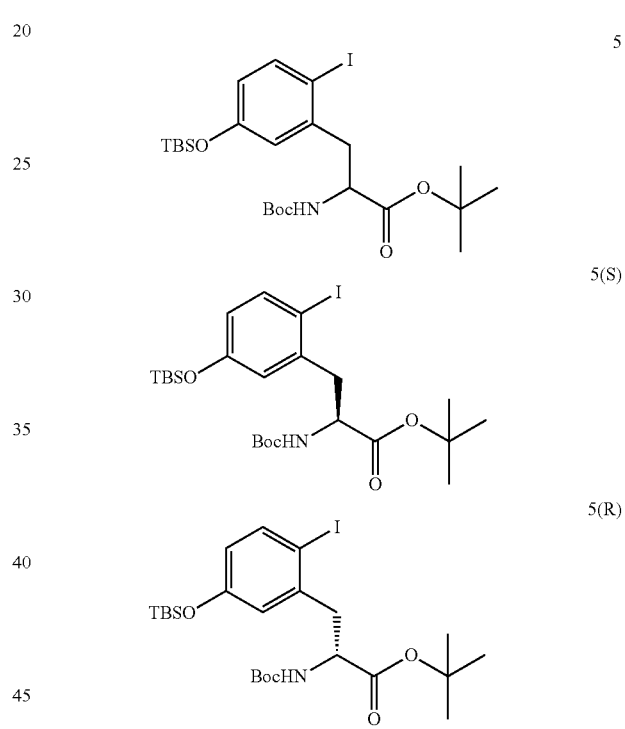

Compound 5 obtained in the above Example 1(4) was resolved by HPLC in the following condition using a chiral column.

Column: CHIRALPAC IA 20 mmφ×250 mm, manufactured by Daicel Corporation

Flow speed: 13 mL/min

Column oven temperature: 25° C.

Detection light wave-length: 233 nm

Eluent: hexane/ethanol=100/1

HPLC retention time: 5(S)—11.46 min, 5(R)—8.12 min

Column: CHIRALPAC IA 4.6 mmφ×250 mm, manufactured by Daicel Corporation

Flow speed: 0.8 mL/min

Column oven temperature: 25° C.

Detection light wave-length: 233 nm

Eluent: hexane/ethanol=99/1

Example 12

Production of Optically-Active Compound 7

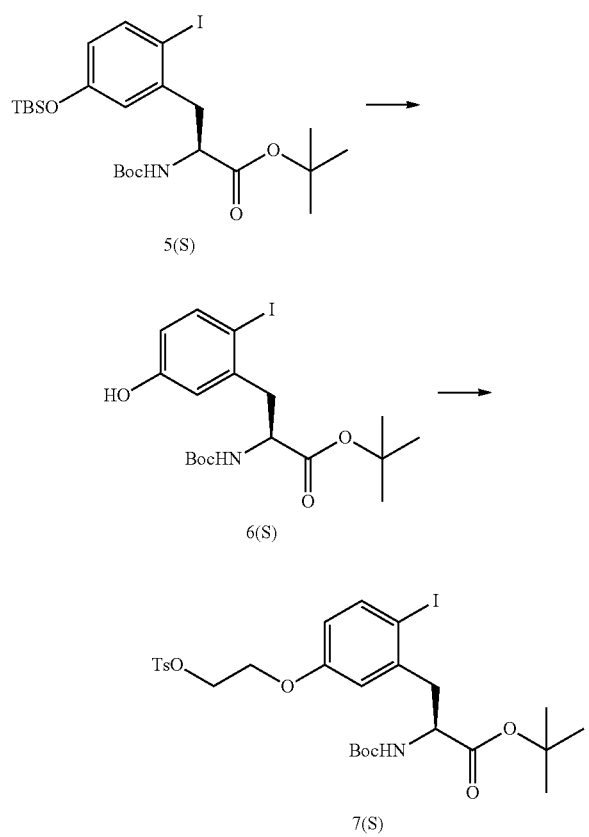

(1) Deprotection of Phenolic Hydroxy Group

Optically-active Compound 6(S) or optically-active Compound 6(R) was synthesized similarly to the synthesis route described in the above Example 1(5) except that optically-active Compound 5(S) or optically-active Compound 5(R) obtained in the above Example 11 was used instead of racemic Compound 5.

(2) O-Alkylation

Optically-active Compound 7(S) (99.7% ee) or optically-active Compound 7(R) (99.7% ee) was synthesized similarly to the synthesis route described in the above Example 2 except that optically-active Compound 6(S) or optically-active Compound 6(R) obtained in the above (1) was used instead of Compound 6.

HPLC retention time: 7(S)—12.94 min, 7(R)—9.33 min

Column: CHIRALPAC IA 4.6 mmϕ×250 mm, manufactured by Daicel Corporation

Flow speed: 0.8 mL/min

Column oven temperature: 25° C.

Detection light wave-length: 254 nm

Eluent: hexane/ethanol=60/40

Example 13

O-Alkylation

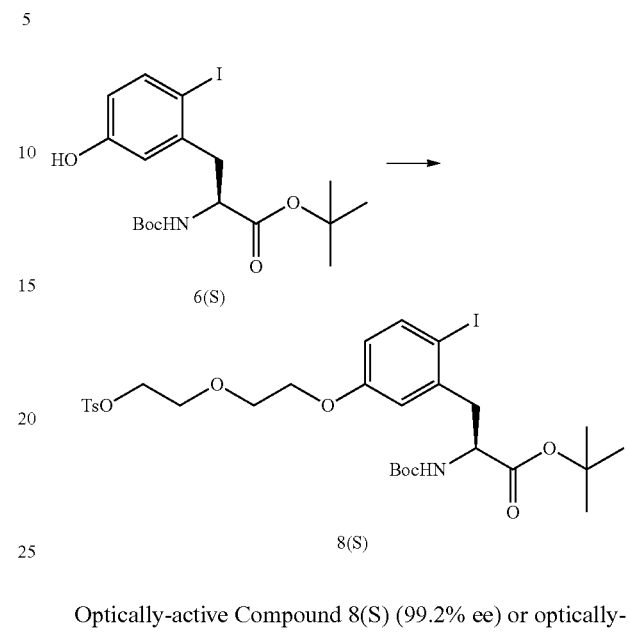

Optically-active Compound 8(S) (99.2% ee) or optically-active Compound 8(R) (99.3% ee) was synthesized similarly to the synthesis route described in the above Example 7 except that optically-active Compound 6(S) or 6(R) was used instead of Compound 6.

HPLC retention time: 8(S)—7.09 min, 8(R)—6.35 min

Column: CHIRALPAC IB 4.6 mmϕ×250 mm, manufactured by Daicel Corporation

Flow speed: 1.0 mL/min

Column oven temperature: 25° C.

Detection light wave-length: 254 nm

Eluent: hexane/ethanol=80/20

Example 14

Synthesis of Bromo Compound

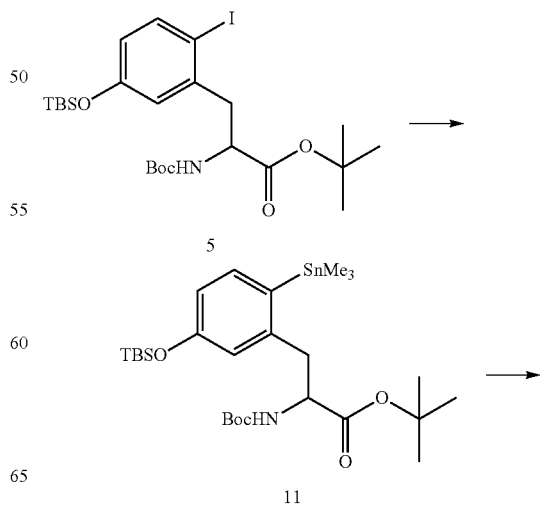

-continued

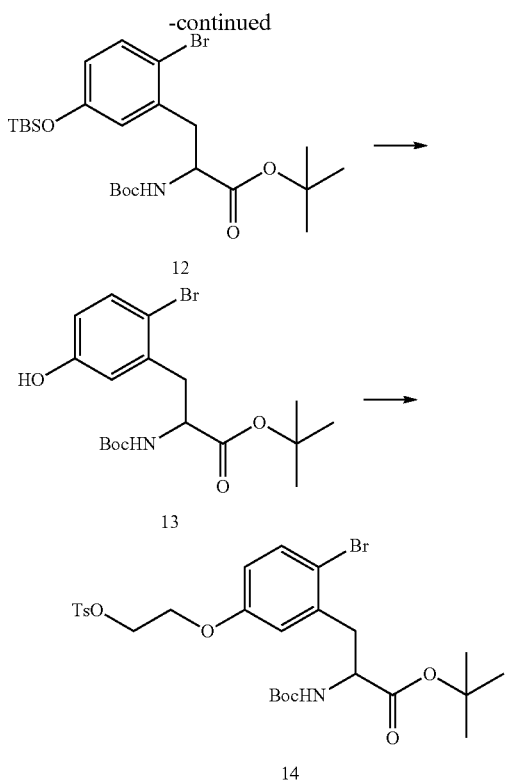

(1) Sn-Ization Reaction to Synthesize Compound 11

To deaerate toluene (2 mL) solution of Compound 5 (100 mg, 0.17 mmol) obtained in the above Example 1(4), tetrakis(triphenylphosphine) palladium (60 mg, 0.05 mmol) and lithium chloride (37 mg, 0.87 mmol), hexamethyldistannane (72 μL, 0.35 mmol) was added under argon atmosphere. The mixture was heated at 100° C. for 6 hours. The mixture was cooled, and then filtered using Celite. The filtrate was concentrated. Compound 11 was obtained by purifying from the residue with silica gel column chromatography (66.3 mg, 62%).

$^1$H-NMR (400 MHz, CDCl$_3$, TMS) δ7.27 (d, J=7.6 Hz, 1H), 6.71 (m, 2H), 4.83 (m, 1H), 4.36 (m, 1H), 3.04 (m, 1H), 2.89 (m, 1H), 1.45 (s, 9H), 1.39 (s, 9H), 0.99 (s, 9H), 0.34 (s, 9H), 0.21 (s, 6H)

(2) Bromination to Synthesize Compound 12

The methanol/diethyl ether solution (1/1, 7 mL) of Compound 11 (20 mg, 0.03 mmol) obtained in the above (1) was cooled to −70° C., and methanol (2 mL) solution of bromine (1.6 μL, 0.03 mmol) was added thereto. After 30 minutes, sodium thiosulfate aqueous solution was added thereto. The mixture was stirred at room temperature. Extraction was carried out with ethyl acetate. The organic layer was washed with saturated saline, and then dried over anhydrous sodium sulfate. After the organic layer was filtered, the filtrate was concentrated under reduced pressure. Compound 12 was obtained by purifying from the residue with silica gel column chromatography (17 mg, 97%).

$^1$H-NMR (400 MHz, CDCl$_3$, TMS) δ7.36 (d, J=8.7 Hz, 1H), 6.73 (s, 1H), 6.59 (dd, J=8.7 Hz and 2.7 Hz, 1H), 5.03 (m, 1H), 4.50 (m, 1H), 3.20 (m, 1H), 3.00 (m, 1H), 1.42 (s, 9H), 1.40 (s, 9H), 0.98 (s, 9H), 0.19 (s, 6H)

(3) Deprotection of Phenolic Hydroxy Group to Synthesize Compound 13

Compound 12 (15 mg, 0.03 mmol) obtained in the above (2) was dissolved in THF (0.1 mL). To the solution, TBAF (42 μL, 1M THF solution) was added at 0° C. The mixture was stirred for 1 hour. After the reaction mixture was filtered, the filtrate was concentrated under reduced pressure to obtain Compound 13 (amount: 11 mg).

$^1$H-NMR (400 MHz, CDCl$_3$, TMS) δ7.37 (d, J=8.7 Hz, 1H), 6.79 (s, 1H), 6.63 (m, 1H), 5.10 (m, 1H), 4.51 (m, 1H), 3.18 (m, 1H), 3.00 (m, 1H), 1.43 (s, 9H), 1.40 (s, 9H)

(4) O-Alkylation Step to Synthesize Compound 14

Anhydrous acetone (40 mL) solution of Compound 13 (2.0 g, 4.8 mmol) obtained in the above (3), potassium carbonate (3.3 g, 24.0 mol) and ethyleneglycol bis(p-toluenesulfonate) (5.3 g, 14.4 mmol) was heated to reflux for 23 hours. The reaction mixture was cooled, and then diluted with water. Extraction was carried out with ethyl acetate (about 50 mL) two times. The combined organic layers was washed with water and saturated saline, and dried over sodium sulfate. After filtration, the filtrate was concentrated. Compound 14 was obtained by purifying from the residue with silica gel column chromatography (2.19 g, 74%).

$^1$H-NMR (400 MHz, CDCl$_3$, TMS) δ7.82 (dt, J=8.4 Hz and 1.9 Hz, 2H), 7.39 (d, J=8.8 Hz, 1H), 7.36 (d, J=7.6 Hz, 2H), 6.71 (s, 1H), 6.56 (m, 1H), 5.04 (m, 1H), 4.51 (m, 1H), 4.34 (m, 2H), 4.11 (m, 2H), 3.19 (dd, J=14.2 Hz and 5.9 Hz, 1H), 2.99 (m, 1H), 2.47 (s, 3H), 1.42 (s, 9H), 1.38 (s, 9H)

Example 15

Optical Resolution of Racemic Compound 14

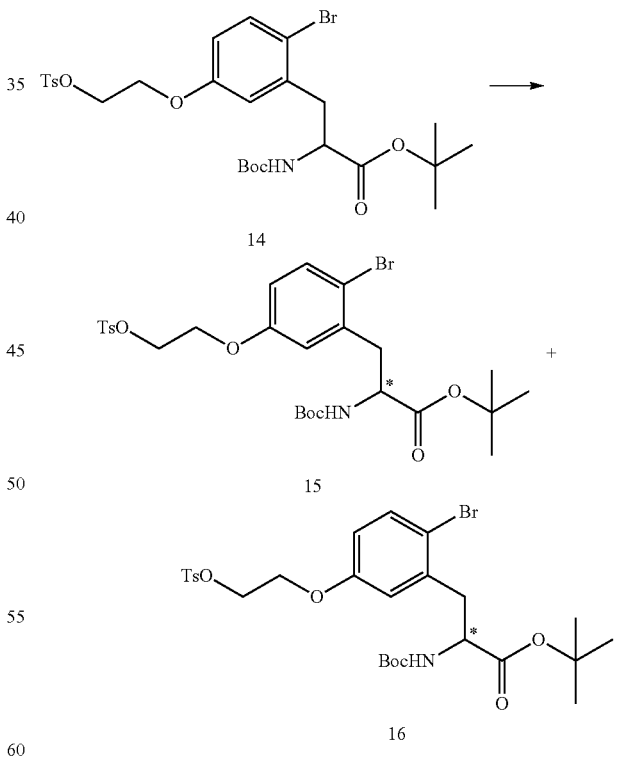

Racemic Compound 14 obtained in the above Example 14 was resolved by HPLC in the following condition using a chiral column. Optically-active Compound 15 (99.7% ee) and optically-active Compound 16 (99.7% ee) were obtained by recrystallization from the HPLC product in hexane/ethyl acetate.

Column: CHIRALPAC IA 20 mmϕ×250 mm, manufactured by Daicel Corporation
Flow speed: 13 mL/min
Column oven temperature: 25° C.
Detection light wave-length: 254 nm
Eluent: hexane/ethanol=7/3
HPLC retention time: Compound 15—11.56 min
Compound 16—15.12 min
Column: CHIRALPAC IA 4.6 mmϕ×250 mm, manufactured by Daicel Corporation
Flow speed: 1.0 mL/min
Column oven temperature: 25° C.
Detection light wave-length: 254 nm
Eluent: hexane/ethanol=70/30

Example 16

Deprotection Reaction

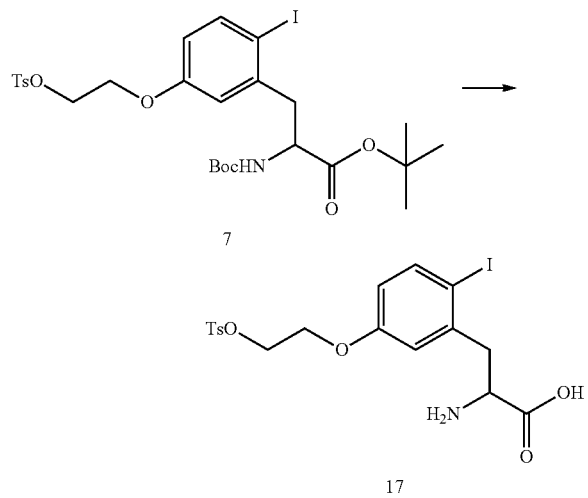

To dichloromethane (0.8 mL) solution of Compound 7 (100 mg, 0.15 mmol) obtained in the above Example 2, trifluoroacetic acid (340 μL) was added. The mixture was stirred at room temperature for 1 day. Then, the reaction mixture was concentrated, and water and ammonia water were added thereto. The precipitated solid was separated by filtration and washed with water to obtain Compound 17 (45 mg, 59%).

$^1$H-NMR (400 MHz, DCl/H$_2$O, DSS) δ7.78 (m, 3H), 7.39 (d, J=8.7 Hz, 2H), 6.80 (d, J=3.2 Hz, 1H), 6.55 (dd, J=8.7 Hz and 3.2 Hz, 1H), 4.51 (t, J=4.1 Hz, 2H), 4.40 (t, J=7.8 Hz, 1H), 4.28 (m, 2H), 3.45 (m, 1H), 3.27 (m, 1H), 2.43 (s, 3H)

Example 17

Inhibitory Activity Test Against Melatonin MT$_1$ Receptor

An inhibitory activity of the tyrosine derivative of the present invention against a melatonin MT$_1$ receptor was evaluated. Specifically, human recombinant melatonin MT$_1$ receptors expressed in CHO-K1 cells were used in modified HEPES buffer pH 7.4. The tyrosine derivative obtained in the above Example 8 was preincubated with 0.025 mg/mL of membranes of the cell and 1 μM of guanosine diphosphate in modified HEPES buffer (pH 7.4) at 25° C. for 20 minutes, then SPA, i.e. Scintillation proximity assay, beads were added thereto. The mixture was preincubated at 30° C. for 60 minutes. The reaction was initiated by adding 0.3 nM of [$^{35}$S] GTPγS and incubating the mixture for 30 minutes, and the test compound-induced inhibition of 0.1 nM 2-iodomelatonin-induced increase of [$^{35}$S]GTPγS binding response was measured.

As a result, the tyrosine derivative obtained in the above Example 8 inhibited the binding between a melatonin MT$_1$ receptor and [$^{35}$S]GTPγS which was accelerated by 2-iodomelatonin by 33%; therefore, it was experimentally demonstrated that the tyrosine derivative of the present invention is an antagonist against a melatonin MT$_1$ receptor.

The invention claimed is:

1. A tyrosine derivative of the following formula (I):

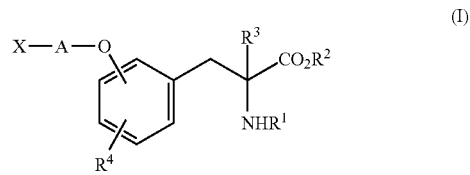

wherein
R$^1$ is a hydrogen atom or a protective group for the amino group;
R$^2$ is a hydrogen atom or a protective group for the carboxy group;
R$^3$ is a hydrogen atom or a C$_{1-6}$ alkyl group;
R$^4$ is a halogen atom, a hydroxy group, a C$_{1-6}$ alkyl group, a C$_{1-6}$ halogenated alkyl group, an amino group, a mono (C$_{1-6}$ alkyl)amino group, a di(C$_{1-6}$ alkyl)amino group, an aryl group optionally having substituent α, a heterocyclic group optionally having substituent α, a C$_{1-6}$ alkoxy group, a C$_{1-6}$ alkylthio group, a C$_{1-6}$ halogenated alkoxy group or a C$_{7-13}$ aralkyloxy group optionally having substituent α;
A is —(CH$_2$)$_l$—[Z(CH$_2$)$_m$]$_n$— wherein Z is an amino group, an ether group, a thioether group, a carbonyl group, a thionyl group, an ester group, an amide group, a urea group or a thiourea group; l is an integer of not less than 1 and not more than 6; m is an integer of not less than 1 and not more than 4; and n is an integer of not less than 0 and not more than 4;
X is a leaving group selected from the group consisting of a chlorine atom, a bromine atom, an iodine atom, a methanesulfonyloxy group, a trifluoromethanesulfonyloxy group, a chloromethanesulfonyloxy group, an ethanesulfonyloxy group, a benzenesulfonyloxy group and a toluenesulfonyloxy group;
substituent α is one or more substituents selected from the group consisting of a halogen atom, a hydroxy group, a cyano group, a thiol group, an amino group, a mono(C$_{1-6}$ alkyl)amino group, a di(C$_{1-6}$ alkyl)amino group, a C$_{1-6}$ alkyl group, a C$_{1-6}$ alkoxy group, a C$_{1-6}$ halogenated alkyl group and a C$_{1-6}$ alkylthio group;
provided that the position of R$^4$ is para to the position of the X-A-O— group.

2. The tyrosine derivative according to claim 1, of the following formula (I'):

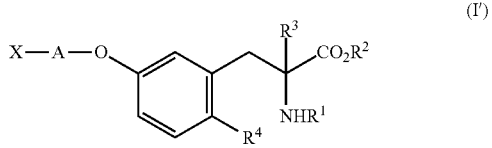

wherein $R^1$ to $R^4$, A and X are the same as the above.

3. The tyrosine derivative according to claim 1, wherein $R^4$ is a halogen atom, a hydroxy group, an aryl group optionally having substituent α, a heterocyclic group optionally having substituent α or a $C_{1-6}$ alkoxy group.

4. The tyrosine derivative according to claim 2, wherein $R^4$ is a halogen atom, a hydroxy group, an aryl group optionally having substituent α, a heterocyclic group optionally having substituent α or a $C_{1-6}$ alkoxy group.

5. The tyrosine derivative according to claim 1, wherein $R^4$ is a bromine atom or an iodine atom.

6. The tyrosine derivative according to claim 2, wherein $R^4$ is a bromine atom, or an iodine atom.

7. The tyrosine derivative according to claim 3, wherein $R^4$ is a bromine atom or an iodine atom.

8. The tyrosine derivative according to claim 4, wherein $R^4$ is a bromine atom or an iodine atom.

9. The tyrosine derivative according to claim 1, wherein A is $—(CH_2)_l—[O(CH_2)_m]_n—$.

10. The tyrosine derivative according to claim 2, wherein A is $—(CH_2)_l[O(CH_2)_m]_n—$.

11. The tyrosine derivative according to claim 3, wherein A is $—(CH_2)_l[O(CH_2)_m]_n—$.

12. The tyrosine derivative according to claim 4, wherein A is $—(CH_2)_l—[O(CH_2)_m]_n—$.

13. The tyrosine derivative according to claim 5, wherein A is $—(CH_2)_l—[O(CH_2)_m]_n—$.

14. The tyrosine derivative according to claim 6, wherein A is $—(CH_2)_l—[O(CH_2)_m]_n—$.

15. The tyrosine derivative according to claim 7, wherein A is $—(CH_2)_l—[O(CH_2)_m]_n—$.

16. The tyrosine derivative according to claim 8, wherein A is $—(CH_2)_l—[O(CH_2)_m]_n—$.

17. A method for producing a tyrosine derivative of the following formula (III):

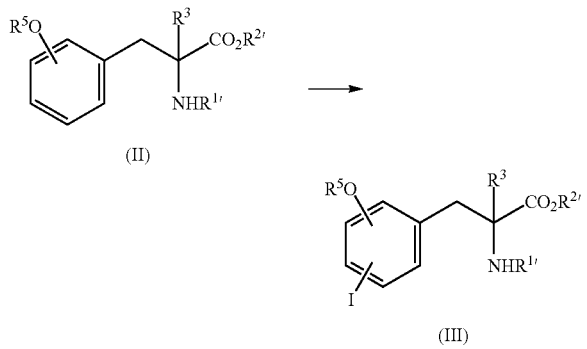

wherein $R^{1\prime}$ is a protective group of the amino group; $R^{2\prime}$ is a protective group of the carboxy group; $R^3$ is a hydrogen atom or a $C_{1-6}$ alkyl group; $R^5$ is a protective group of the phenolic hydroxy group; provided that the position of the iodine atom is para to the position of the $R^5O$-group, comprising the step of reacting the compound of formula (II) with an iodination reagent at −50° C. or lower.

18. The production method according to claim 17, wherein a combination of a molecular iodine and an iodination reaction accelerator is used as the iodination reagent.

19. The production method according to claim 18, wherein silver trifluoroacetate or silver acetate is used as the iodination reaction accelerator.

20. A method for producing a tyrosine derivative of the following formula (I):

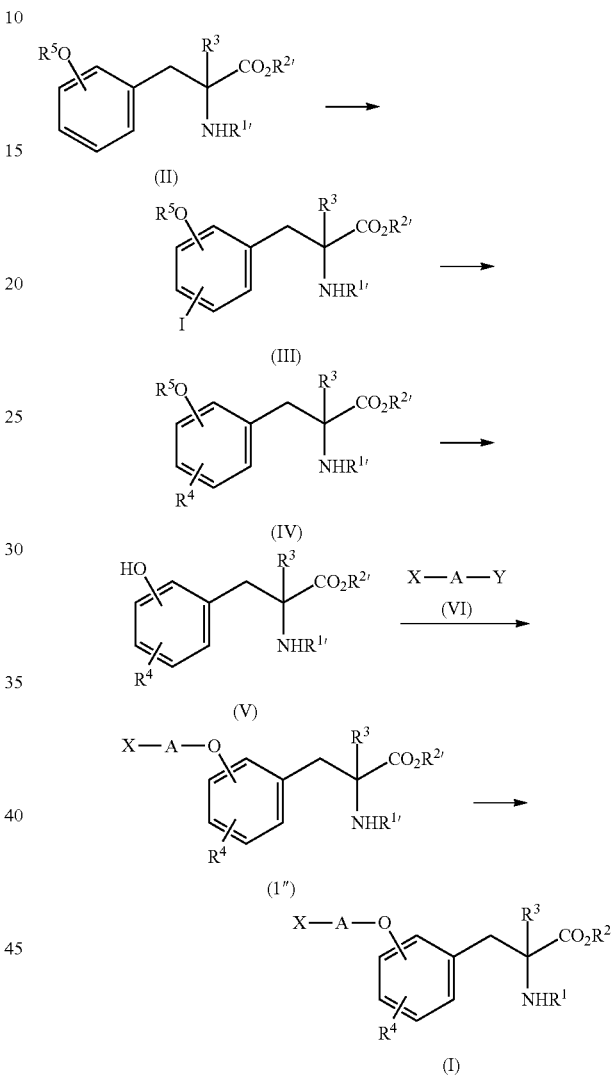

wherein
$R^1$ is a hydrogen atom or a protective group for the amino group;
$R^2$ is a hydrogen atom or a protective group for the carboxy group;
$R^{1\prime}$ is a protective group for the amino group;
$R^{2\prime}$ is a protective group for the carboxy group;
$R^3$ is a hydrogen atom or a $C_{1-6}$ alkyl group;
$R^4$ is a halogen atom, a hydroxy group, a $C_{1-6}$ alkyl group, a $C_{1-6}$ halogenated alkyl group, an amino group, a mono($C_{1-6}$ alkyl)amino group, a di($C_{1-6}$ alkyl)amino group, an aryl group optionally having substituent α, a heterocyclic group optionally having substituent α, a $C_{1-6}$ alkoxy group, a $C_{1-6}$ alkylthio group, a $C_{1-6}$ halogenated alkoxy group or a $C_{7-13}$ aralkyloxy group optionally having substituent α;

$R^5$ is a protective group of the phenolic hydroxy group;

A is $-(CH_2)_l-[Z(CH_2)_m]_n-$ wherein Z is an amino group, an ether group, a thioether group, a carbonyl group, a thionyl group, an ester group, an amide group, a urea group or a thiourea group; l is an integer of not less than 1 and not more than 6; m is an integer of not less than 1 and not more than 4; n is an integer of not less than 0 and not more than 4;

X is a leaving group selected from the group consisting of a chlorine atom, a bromine atom, an iodine atom, a methanesulfonyloxy group, a trifluoromethanesulfonyloxy group, a chloromethanesulfonyloxy group, an ethanesulfonyloxy group, a benzenesulfonyloxy group and a toluenesulfonyloxy group;

Y is a hydroxy group or a leaving group selected from the group consisting of a chlorine atom, a bromine atom, an iodine atom, a methanesulfonyloxy group, a trifluoromethanesulfonyloxy group, a chloromethanesulfonyloxy group, an ethanesulfonyloxy group, a benzenesulfonyloxy group and a toluenesulfonyloxy group;

substituent α is one or more substituents selected from the group consisting of a halogen atom, a hydroxy group, a cyano group, a thiol group, an amino group, a mono($C_{1-6}$ alkyl)amino group, a di($C_{1-6}$ alkyl)amino group, a $C_{1-6}$ alkyl group, a $C_{1-6}$ alkoxy group, a $C_{1-6}$ halogenated alkyl group and a $C_{1-6}$ alkylthio group;

provided that the position of the iodine atom or $R^4$ is para to the position of the $R^5O$-group, the hydroxy group or X-A-O— group;

comprising the steps of:

reacting the compound of formula (II) with an iodination reagent at −50° C. or lower in order to obtain the compound of formula (III);

transforming the iodine atom of the compound (III) to $R^4$ when $R^4$ of the compound (IV) is not an iodine atom in order to obtain the compound of formula (IV);

removing the protective group of the phenolic hydroxy group of the compound (IV) in order to obtain the compound of formula (V);

reacting the compound (V) with the compound of formula (VI) in order to obtain the compound of formula (I″); and removing the protective group of at least one of the amino group or the carboxy group if necessary in order to obtain the compound of formula (I).

* * * * *